US011189133B2

(12) United States Patent
Neely et al.

(10) Patent No.: US 11,189,133 B2
(45) Date of Patent: *Nov. 30, 2021

(54) SYSTEM AND METHOD OF WAGERING ON A PLURALITY OF EVENTS

(71) Applicant: Exacta Systems, LLC, Nashville, TN (US)

(72) Inventors: Patrick Neely, Jupiter, FL (US); Glen M. Rose, Wellington, FL (US); Jeremy F. Stein, Wellington, FL (US); Jefferson C. Lind, Austin, TX (US); Joseph R. Enzminger, Austin, TX (US); Thomas L. Aronson, West Palm Beach, FL (US)

(73) Assignee: Exacta Systems, LLC, Boynton Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/541,175

(22) PCT Filed: Dec. 28, 2015

(86) PCT No.: PCT/US2015/067688
§ 371 (c)(1),
(2) Date: Jun. 30, 2017

(87) PCT Pub. No.: WO2016/111870
PCT Pub. Date: Jul. 14, 2016

(65) Prior Publication Data
US 2017/0372561 A1    Dec. 28, 2017

Related U.S. Application Data

(60) Provisional application No. 62/100,242, filed on Jan. 6, 2015.

(51) Int. Cl.
*G07F 17/32* (2006.01)

(52) U.S. Cl.
CPC ...... *G07F 17/3288* (2013.01); *G07F 17/3211* (2013.01); *G07F 17/3225* (2013.01);
(Continued)

(58) Field of Classification Search
CPC .... G07F 17/32; G07F 17/3225; G07F 17/323; G07F 17/3244; G07F 17/3288
(Continued)

(56) References Cited

U.S. PATENT DOCUMENTS

| 4,624,463 A | 11/1986 | Glennon |
| 5,830,068 A * | 11/1998 | Brenner et al. ......... G07F 17/32 463/42 |

(Continued)

FOREIGN PATENT DOCUMENTS

| GB | 120946 A | 11/1918 |
| GB | 2 229 565 A | 9/1990 |

(Continued)

OTHER PUBLICATIONS

International Search Report and Written Opinion issued in PCT/US2014/025546, dated Sep. 1, 2014, 12 pgs.

*Primary Examiner* — Chase E Leichliter
(74) *Attorney, Agent, or Firm* — Woodard Emhardt Henry Reeves & Wagner LLP

(57) ABSTRACT

A system and method for concurrently wagering on multiple past events such as sports events that may include retrieving data about multiple events that occurred in the past that included multiple participants. The data may include information about the participants as well as pre-event rankings, and final or post-event rankings ordering the results with respect to other participants in the same event. A user may adjust the pre-event rankings or accept them as-is. The user's rankings for the participants of the events may be submitted, and a prize calculated based on the difference (Continued)

between the predicted rankings submitted by the user, and the final rankings of the participants based on actual past events. Various terminals, terminal configurations, and user interface aspects are also disclosed.

50 Claims, 7 Drawing Sheets

(52) U.S. Cl.
CPC ...... *G07F 17/3244* (2013.01); *G07F 17/3246* (2013.01); *G07F 17/3272* (2013.01)

(58) Field of Classification Search
USPC .......................................................... 463/28
See application file for complete search history.

(56) References Cited

U.S. PATENT DOCUMENTS

| | | | |
|---|---|---|---|
| 6,120,376 A * | 9/2000 | Cherry | G07F 17/32 273/139 |
| 6,152,822 A * | 11/2000 | Herbert | G07F 17/32 463/16 |
| 6,309,307 B1 * | 10/2001 | Krause | A63F 1/00 463/16 |
| 6,331,148 B1 * | 12/2001 | Krause | A63F 1/00 463/16 |
| 6,358,150 B1 * | 3/2002 | Mir | G07F 17/32 463/28 |
| 6,450,887 B1 * | 9/2002 | Mir | G06Q 50/34 463/25 |
| 6,658,396 B1 | 12/2003 | Tang et al. | |
| 7,291,070 B2 | 11/2007 | Gatto et al. | |
| 7,793,789 B2 | 9/2010 | Psaradellis | |
| 7,883,411 B2 * | 2/2011 | Vlazny et al. | G07F 17/32 463/28 |
| 7,951,002 B1 | 5/2011 | Brosnan | |
| 8,277,319 B2 | 10/2012 | Gong | |
| 8,342,959 B2 | 1/2013 | Mahaffey et al. | |
| 8,473,242 B1 | 6/2013 | Hubbard et al. | |
| 8,636,571 B2 * | 1/2014 | Miller | G07F 17/3288 463/6 |
| 9,947,174 B2 * | 4/2018 | Rangarajan | G07F 17/3244 |
| 10,997,825 B2 * | 5/2021 | Neely | G07F 17/3272 |
| 2002/0052230 A1 | 5/2002 | Martinek et al. | |
| 2002/0107072 A1 | 8/2002 | Giobbi | |
| 2003/0109310 A1 | 6/2003 | Heaton et al. | |
| 2003/0151554 A1 | 8/2003 | McCarthy | |
| 2003/0171149 A1 | 9/2003 | Rothschild | |
| 2004/0193469 A1 * | 9/2004 | Amaitis | G06Q 99/00 705/500 |
| 2004/0204234 A1 | 10/2004 | Walker et al. | |
| 2004/0229671 A1 * | 11/2004 | Stronach | G07F 17/3288 463/6 |
| 2005/0113172 A1 | 5/2005 | Gong | |
| 2005/0170886 A1 * | 8/2005 | Miller | G07F 17/3288 463/28 |
| 2005/0176499 A1 * | 8/2005 | Stronach | G07F 17/3258 463/27 |
| 2006/0084483 A1 * | 4/2006 | Shin | G07F 17/3288 463/6 |
| 2006/0154718 A1 | 7/2006 | Willyard et al. | |
| 2006/0246990 A1 * | 11/2006 | Downes | G07F 17/32 463/16 |
| 2006/0247035 A1 | 11/2006 | Rowe et al. | |
| 2006/0258432 A1 * | 11/2006 | Packer | G07F 17/332 463/16 |
| 2007/0026940 A1 * | 2/2007 | Cannella | G07F 17/3288 463/28 |
| 2007/0155471 A1 * | 7/2007 | Powell | G07F 17/3286 463/19 |
| 2007/0197281 A1 | 8/2007 | Stronach | |
| 2007/0256988 A1 | 11/2007 | Psaradellis | |
| 2007/0290878 A1 | 12/2007 | Maggio | |
| 2008/0227532 A1 | 9/2008 | Gelman | |
| 2008/0248846 A1 * | 10/2008 | Stronach | G07F 17/3288 463/6 |
| 2009/0011813 A1 * | 1/2009 | Saffron | G07F 17/32 463/17 |
| 2009/0298576 A1 | 12/2009 | Nguyen | |
| 2010/0120538 A1 * | 5/2010 | Dewitt | G07F 17/3223 463/42 |
| 2010/0173699 A1 | 7/2010 | Gagner et al. | |
| 2010/0210351 A1 * | 8/2010 | Berman | G07F 17/3246 463/25 |
| 2011/0053684 A1 * | 3/2011 | Attwood | G07F 17/32 463/28 |
| 2011/0093295 A1 | 4/2011 | Mankad et al. | |
| 2011/0223989 A1 * | 9/2011 | Owen | G07F 17/32 463/25 |
| 2011/0250937 A1 | 10/2011 | Hubbard et al. | |
| 2012/0034961 A1 * | 2/2012 | Berman | G07F 17/3288 463/6 |
| 2013/0053991 A1 * | 2/2013 | Ferraro III | G06Q 90/00 700/93 |
| 2013/0281183 A1 | 10/2013 | Borissov et al. | |
| 2014/0011573 A1 * | 1/2014 | Amaitis | G07F 17/3288 463/25 |
| 2014/0066188 A1 * | 3/2014 | Brooks | G07F 17/326 463/28 |
| 2014/0066189 A1 * | 3/2014 | Brooks | G07F 17/3288 463/28 |
| 2014/0287805 A1 | 9/2014 | Herbert | |
| 2015/0262452 A1 * | 9/2015 | Corckran | G07F 17/3295 463/28 |
| 2015/0302698 A1 * | 10/2015 | Keech | G07F 17/3225 463/16 |
| 2015/0364009 A1 * | 12/2015 | Keech | G07F 17/3227 463/28 |
| 2016/0189483 A1 * | 6/2016 | Ballman | G07F 17/3288 463/28 |
| 2017/0372561 A1 * | 12/2017 | Aronson | G07F 17/3225 |
| 2019/0251789 A1 * | 8/2019 | Waters | G07F 17/3244 |
| 2019/0325707 A1 * | 10/2019 | Aronson | G07F 17/3211 |

FOREIGN PATENT DOCUMENTS

| | | |
|---|---|---|
| GB | 212573 | 7/2002 |
| GB | 312340 | 7/2003 |
| GB | 2 398 515 A | 8/2004 |
| WO | WO 2002/49730 A1 | 6/2002 |

* cited by examiner

SYSTEM AND METHOD OF WAGERING ON A PLURALITY OF EVENTS

BACKGROUND

The disclosed system and related methods of operation generally relate to betting on multiple past events, concurrently, such as, for example, multiple horse races, dog races, automobile races, or any other suitable event, in a pari-mutuel environment.

SUMMARY

Disclosed is a method of wagering on past events that includes controlling an input device to accept a wager amount defining an amount of a currency to wager, wherein the input device is controlled by a processor. The processor may be used to initiate a transfer of the amount of currency to wager into a common prize pool, and may query a database to automatically retrieve data about multiple events that occurred in the past and included multiple participants. The data about the events may include a final ranking for respective multiple participants ranking the participants with respect to other participants who competed in the same event. The method may further include controlling the input device to accept predicted rankings for the participants of the events using the processor. These predicted rankings may indicate what a user believes the final rankings will be for the multiple participants competing in their respective events. The processor may be used to calculate a final score based on the similarity between the predicted rankings and the final rankings of the participants in their respective events. The processor may also calculate a prize which may be calculated based on the final score and the wager input. The prize may include or consist of an item such as a piece of jewelry or a currency amount. The processor may be used to initiate a transfer of the prize out of the common prize pool when the prize amount is greater than zero.

In another aspect, the method may include calculating a pre-event ranking for the participants using the processor. The pre-event ranking may be calculated based on individual odds of the participants finishing with a particular ranking for their respective events. The individual odds may have been calculated before the respective events occurred in the past, and may be included in the data about the events.

In another example, a method of wagering on past events includes entering an amount to be wagered using an input device coupled to a processor, wherein the processor may be configured to initiate a transfer of the amount to be wagered into a common prize pool. The method may also include entering a separate predicted ranking for multiple participants of multiple events (such as sporting events) completed in the past using the input device coupled to the processor, wherein data about the multiple participants is retrieved from a database using the processor, wherein the predicted rankings are entered by changing an initial ranking calculated by the processor based on the probability of each participant obtaining the highest ranking among all participants for a particular event, and wherein the probability of each participant obtaining the highest final ranking in their respective event was calculated before the multiple events took place and stored in the database as part of the data about the multiple participants. The method may also include requesting the calculation of a final prize amount using the input device, wherein the final prize amount is a currency amount calculated using the processor based on the difference between the predicted and actual final rankings of the participants in the multiple selected events that occurred in the past.

As disclosed herein, the past events may be sporting events such as horse races, wherein the participants are horses, wherein the predicted ranking is the predicted order of finish for the horses in each of the horse races, and where the final ranking is the actual order of finish for the horses competing in their respective races.

In another aspect, the methods disclosed herein may include calculating the final score by optionally generating a wager result. The wager result may be generated by comparing the predicted ranking to the final ranking for each participant of each event using the processor. A probability of occurrence may be optionally assigned to each wager result using the processor. The processor may also query the data about the events to determine the frequency of the outcome represented by the wager result. The wager result may optionally include a first identifier for each participant in each event wherein the final ranking and predicted ranking match, and a second identifier for each participant in each event wherein the final ranking and predicted ranking do not match. The prize amount may be optionally calculated using the probability of occurrence assigned to the wager result, and wherein wager results with a probability below a predetermined threshold result in a zero prize amount.

In another aspect, the data about the multiple events retrieved from the database may be randomly selected from the events stored in the database. The method may also optionally include retrieving multiple events such as two or more events, three or more events, five or more events, or any other suitable number of events greater than one.

In another aspect, the terminal disclosed may include an electronic scanning device configured to accept paper currency or a credit voucher. The electronic scanning device may be configured to operate in conjunction with the input device to enter and accept the amount to be wagered. In another aspect, the electronic scanning device may be a bill or coin acceptor controlled by the processor.

In another aspect, the methods disclosed herein may include using the processor to control a display device to display a video representation of at least one of the multiple events on the display device.

The methods disclosed above may further include requesting the transfer of the final prize amount using the input device, wherein the processor is configured to initiate the transfer of the final prize amount from the common prize pool.

In another aspect, the terminal disclosed herein includes a database which is stored in an electronic storage device mounted within the terminal. The database may optionally be stored in an electronic storage device mounted outside the terminal, and wherein the processor is coupled to the database using a computer network.

In another aspect, the events disclosed are dog races, wherein the participants are dogs, wherein the predicted ranking is the predicted order of finish for the dogs in each of the dog races, and wherein the final ranking is the actual order of finish for the dogs competing in their respective races.

In another aspect, the events disclosed are team competitions, wherein the participants are teams of individual competitors, wherein the predicted ranking is the predicted outcome for the team in each of the team competitions, and wherein the final ranking is the actual outcome for the teams competing in their respective team competitions.

Also disclosed is a system configured to perform some or all of the disclosed methods. The system may have a display device configured to display output to a user, an input device configured to accept input from a user, a processor coupled to a memory, the display device, and the input device, and a computer network accessible by the processor. The processor may be configured to access a database using the computer network. The system may also include an electronic wagering terminal. The display device, processor, and memory may be mounted to the terminal.

Any system disclosed herein may also include a process control module configured to use the processor to initiate a transfer of an amount to be wagered into a common prize pool, and to use the processor to initiate a transfer of a prize amount out of the common prize pool when the prize amount is greater than zero, wherein the common prize pool may be maintained in the database.

A system may further include an event selection engine configured to use the processor to retrieve event data about multiple selected events that occurred in the past from a database, wherein the event data includes data about multiple participants participating in the selected events.

A pre-event ranking module may be included and configured to calculate an initial ranking for each participant using the processor, wherein the initial ranking is calculated using odds of each respective participant completing the event with the highest final ranking determined in the past before the event took place.

A user interface module may be included and configured to control the display device to display the initial rankings using the processor. A scoring module may also be included and configured to calculate a final score based on the similarities or differences between the user selected rankings for the participants and final rankings of the participants using the processor, wherein the final rankings are ranked according to the actual results of the event that occurred in the past. A prize selection module may also be included and configured to calculate the prize amount using the processor, wherein the prize amount may be an item, a currency amount, or any other valuable asset transferred based on the final score and the amount to be wagered.

In another aspect, the user interface module may be configured to accept user input defining user selected rankings, wherein the user selected rankings are defined by changing the initial rankings for at least one participant for at least one of the selected events using the input device.

Further forms, objects, features, aspects, benefits, advantages, and embodiments of the present invention will become apparent from a detailed description and drawings provided herewith.

DETAILED DESCRIPTION

Figure 1:
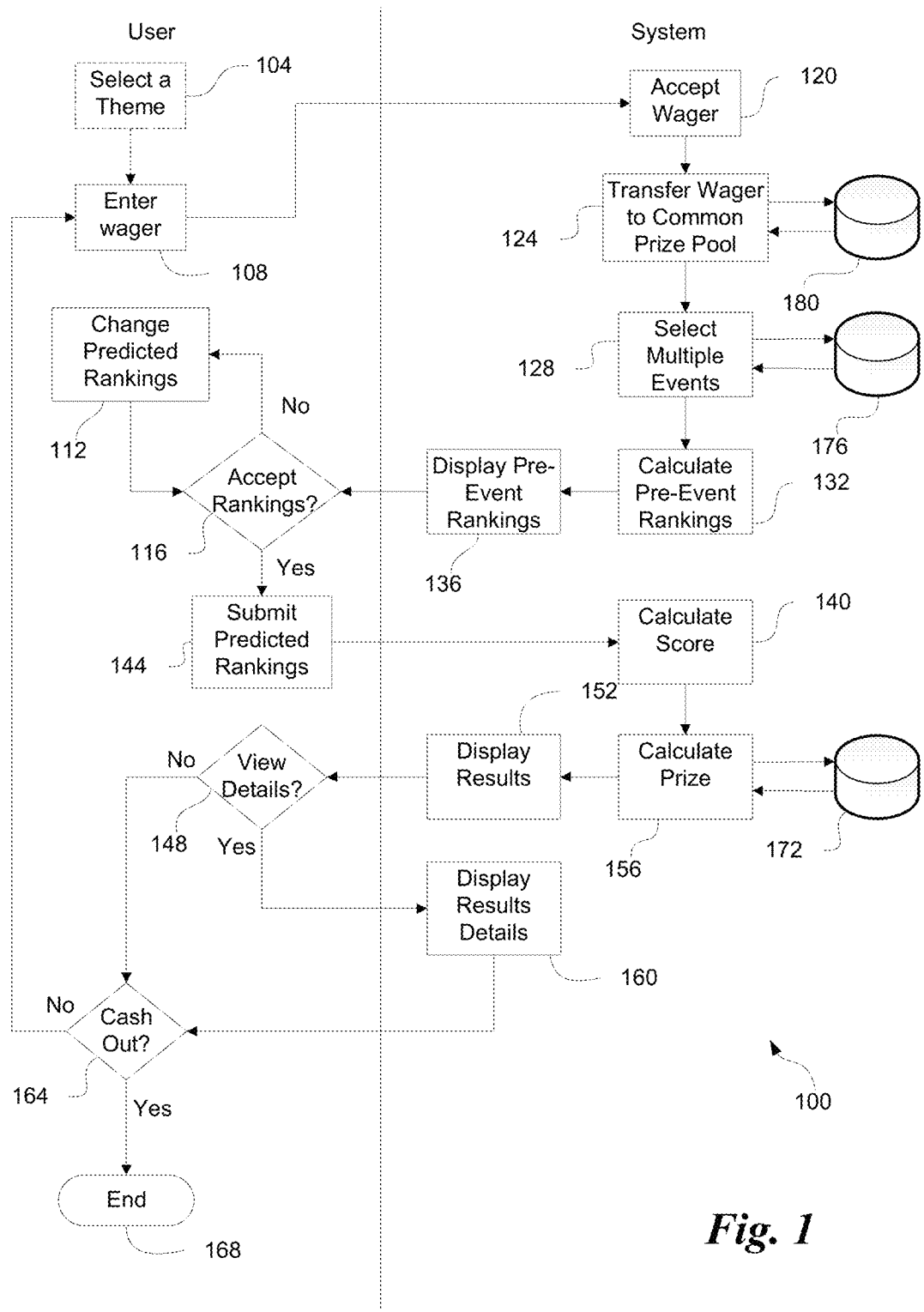
FIG. 1 is flow chart illustrating one example of a method of wagering on multiple past events.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

The reference numerals in the following description have been organized to aid the reader in quickly identifying the drawings where various components are first shown. In particular, the drawing in which an element first appears is typically indicated by the left-most digit(s) in the corresponding reference number. For example, an element identified by a "100" series reference numeral will first appear in FIG. 1, an element identified by a "200" series reference numeral will first appear in FIG. 2, and so on. With reference to the Specification, Abstract, and Claims sections herein, it should be noted that the singular forms "a", "an", "the", and the like include plural referents unless expressly discussed otherwise. As an illustration, references to "a device" or "the device" include one or more of such devices and equivalents thereof.

Disclosed is a system configured to facilitate betting on multiple historical events concurrently. The system may include networked processors or computers (e.g. servers, databases, and wagering terminals) to manage one or more common betting pools in a pari-mutuel wagering environment. The system may optionally include a totalizator for accepting and processing the wagers, making pool allocations, calculating the odds and prices of the wagers, calculating the commission for the operator, and distributing winnings Player prizes may be rewarded based on how closely the player matches the outcome for each participant in each event with the actual outcome for that particular event that occurred in the past.

For example, where players are concurrently betting on the finishing position of horses in multiple horse races that have already occurred, the system can calculate the share of a pari-mutuel pool to award a winning player based on how many finishing positions from the horse races the player correctly predicted. The system may optionally maintain separate math models and separate pari-mutuel wagering pools for different denominations and bet levels offered by each math model.

The disclosed system can also include wagering terminals configured to operate games that may communicate with various servers, databases, and a totalizator to allow players to place pari-mutuel bets on historical events. As disclosed herein elsewhere in further detail, players use a terminal to rank the results for each participant in a past event. These predicted rankings may be assisted by displaying to the user pre-event rankings based on the probability of each participant finishing with the highest ranking. These pre-event rankings may be based on calculations of odds or probabilities that were available to bettors before the event occurred in the past (e.g. published odds based on actual pre-event betting, or on the opinion of experts). The user may alter these rankings according to their own beliefs about the outcome. The system may also provide pre-race handicapping information that was available before the event actually took place in the past to aid the user in making their predictions. The system may also provide handicapping information corresponding to the circumstances of each race (for example the distance, surface, and jockeys) to aid the user in making a wagering decision.

FIG. 1 illustrates one example of a method of betting on multiple events that have already occurred in the past. The user begins by accessing a terminal and optionally selecting a theme at 104 entering a wager at 108. As discussed in further detail herein elsewhere, a terminal may allow a user to enter a wager and place bets using the same physical terminal, or these actions may be taken using separate terminals or other devices.

A wager may be placed by any suitable method such as by an electronic funds transfer or by inserting physical currency into a bill acceptor. For example, the terminal may include a bill acceptor controlled by a processor and configured to accept an amount of currency the player wishes to wager. The processor controlling the bill acceptor may be the same processor controlling the overall terminal, or it may be a separate processor controlling a different system designed to also control the terminal or be a separate processor coupled to the bill acceptor by a computer network. An input device may also be used along with the bill acceptor, or in place of it, to accept a wager amount defining an amount of currency to wager. This input device may be controlled by the processor and mounted in the wagering terminal itself, or it may be included in another terminal separate from the wagering terminal.

The system accepts the wager entered by the user at 120, and transfers the wager, or initiates a transfer of the wager, to a common prize pool stored in a prize pool database at 180. The terminal may, for example, use the processor in the terminal (or another processor) to initiate a transfer of the amount of currency to wager into the common prize pool managed by or stored in database 180.

At 128, the system may use the processor in the terminal (or another processor in the system) to query a database 176 to automatically retrieve data about multiple events that occurred in the past that included multiple participants. The data about the multiple events may be automatically retrieved by any suitable process. For example, the system may randomly select the data from database 176 by using the processor to initiate a random or pseudo-random selection query selecting the events one-by-one with successive queries, or by a single query selecting all the events. Limits may be imposed as well on the number of events retrieved. In one example, data about three events is retrieved. Any suitable number of events may be retrieved and displayed to a user such as two events, four events, five or more events, or ten or more events as well. Three separate databases 180, 176, and 172 are shown in FIG. 1. However, these representations are illustrative only, as the system may store data in a single database containing all the data of database 180, 176, and 172, or the system may store the data in multiple additional databases.

The data about the events may include a final ranking for the respective multiple participants ranking the participants with respect to other participants who competed in the same event. For example, where the events are separate horse races, the participants are horses, and the final ranking for the respective participants in each event is determined by the finishing position in the field. Horses finishing first in the separate races are ranked higher than horses finishing subsequent to the first place finishers. A similar ranking system may be used to rank finishers in other kinds of events such as dog races, automobile races, swimming, track and field events, or other events where participants are ranked based on the order in which they cross a finish line (or put another way, in ascending order of the time it takes for the participants to navigate at least a portion of a particular course or track one or more times).

Other ranking systems may be used, such as rankings based on subjective performance metrics that are assigned by a judge, or panel of judges such as in gymnastics, figure skating, diving, and others. In another example, participants may be ranked in ascending order depending on the number of particular actions that must be taken such as in golf or in some types of target shooting sports using bows or guns. In yet another example, the participants may be teams with multiple individual team members performing various roles during the event such as baseball players or basketball players. In this example, the team maybe ranked in descending order according to points scored, games won in a season, or number of times the team has won or lost against a particular opponent. Other metrics may not involve wins and losses but overall team performance such as the number of home runs hit, the number of three point shots made, and the like. Any suitable statistic collected or generated memorializing the performance of participants in an event may be used to rank the performance of participants in an event.

Database 176 may contain data about multiple events such as sporting events or any other suitable event that occurred in the past that fit specific criteria. For example, the data may include data about horse races such as races with ten horse fields where no horses were scratched from the race, where there were no dead heats, where there were no coupled entries, where all horses finished the race, where all horses had odds of winning (i.e. odds of having the highest final ranking) that were greater than 0 at the time of the race, or where the facility hosting the race was located within the borders of the United States, or any combination thereof. Any other criteria may be imposed. Database 176 may also include race replay information such as video clips, or graphical representations of the results of various events. It may also include charts, graphs, statistical data, and the like explaining predicted results and actual final results for the participants in the events themselves.

The system may optionally calculate a "pre-event" or "initial" ranking at 132 using the processor. This pre-event ranking may be calculated based on the odds of the participants finishing in a particular order for their respective events. These odds may be obtained from database 176 because the respective events have already occurred, and pre-event odds may have been calculated in the past before the events occurred. For example, where the events are horse races, the system may include in the data about the individual races rankings for the horses calculated according to the odds of each particular horse winning the race they ran in. For example, the best (or lowest) odds equal the highest pre-event ranking and continuing in descending order with worst (or highest) odds having the lowest pre-event ranking.

These pre-event odds may be well-known and publicly available before the event, and may therefore be saved in database 176 along with other data about the multiple events retrieved in the query at 128. Pre-event odds generally seek to indicate the outcomes most likely to occur for the participants of an event and may involve the use of computers and odds-making software. In one example, the pre-event odds may be set by entities or individuals including employees of a venue hosting the event, professional handicappers or subject matter experts paid to determine the pre-event odds, or journalists familiar with the type of event, to name a few. In another example, pre-event odds may also be set in whole or in part based on actual bets placed on the outcome of an event.

Pre-event rankings may be displayed to the user by the system at 136 and the user may then be presented with the opportunity to accept the rankings at 116 or reject them. The processor may control an input device to accept predicted rankings for the participants of the events using the processor. These predicted rankings provide users with a way of predicting the final ranking for the multiple participants competing in their respective events. If the user does not accept the rankings, the user may change the predicted rankings at 112 by, for example, using an input device to indicate or select a different ranking for at least one participant in the multiple events displayed. When the user is comfortable with the predicted rankings, the rankings may be submitted at 144. The submitted rankings may then be understood by the system to be the user's wager as to the outcome of the past event.

Using the predicted rankings submitted by the user at 144, the system may calculate a final score or final wager result at 140 using the processor. Any suitable scoring calculation may be used. In one example, the final score is calculated based on the similarity (or the difference) between the predicted rankings and the final rankings of the participants in their respective events. The score may in this example be higher where the predicted rankings more closely match the final rankings for the participants in the event, and proportionally lower as the predicted rankings differ more widely from the final rankings. For example, the final score may generate a wager result by comparing the predicted ranking to the final ranking for each participant of each event using the processor. For example, the wager result may include or define an alphanumeric or other string of indicia where a first identifier (e.g. a "1" other suitable indicia) is included in the wager result for each participant in each event where the final ranking and predicted ranking match, and a second identifier (e.g. a "0" or other suitable indicia) is included in the wager result for each participant in each event where the final ranking and predicted ranking do not match. The system may optionally assign an overall probability of occurrence to the wager result by using the processor to query results data in database 172 to determine the odds of the outcome represented by the wager result. Wager results that are less likely may then receive a higher final score, while wager results that are more likely may receive a lower final score.

A prize amount may be calculated using the processor at 156 using the final score (and/or the wager result if one was calculated) along with the wager entered by the user. The prize amount may be calculated using the probability of occurrence assigned to the wager result and may include querying prize data stored in a prize database 172. A prize amount may then be higher for a wager result that is less likely to occur, and lower for a wager result that is more likely to occur. The system may also be configured with a lowest paying result that operates as a predetermined threshold. Wager results that are below this predetermined threshold may then receive a zero prize amount meaning that the user loses some or all of the wager amount initially entered at 108.

The results may be displayed to the user at 152, where the display may present to the user an option to see additional details for the final results of the events that occurred in the past. The system may then display additional results details at 160 if the user requests to see them at 148. The additional results data may include controlling the display device to display a replay of at least a portion of one or more of the past events. The computer generating this output may include the processor in the wagering terminal itself, or a processor that generated the graphical representation and sent it to the wagering terminal over a computer network. Any suitable additional detail explaining the results for each of the multiple events may be displayed at 160.

The system may then use the processor to initiate a transfer of the prize amount as a currency amount out of the common prize pool and into the users account in the case where the prize amount is greater than zero. This may occur automatically, or based on a prompt provided by the user using an input device such as a keyboard or touchscreen. In another example, the processor initiates a transfer of the prize amount when a user provides input requesting the system to cash out at 164 any prize money the user may have accumulated thus ending the process at 168. If the user does not elect to cash out, the system may present an option to continue with another wager at 108. The user and the system may then interact as disclosed to repeat the betting process any number of times where the user has sufficient funds to wager repeatedly. Multiple users may engage in the actions discussed herein entering money into the common prize pools and withdrawing winnings where they are obtained. In this way, the system is configured to allow users to participate in pari-mutuel betting on multiple past events having multiple participants.

Figure 2:
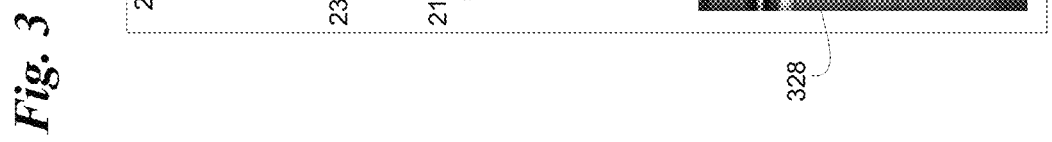
Figure 2:
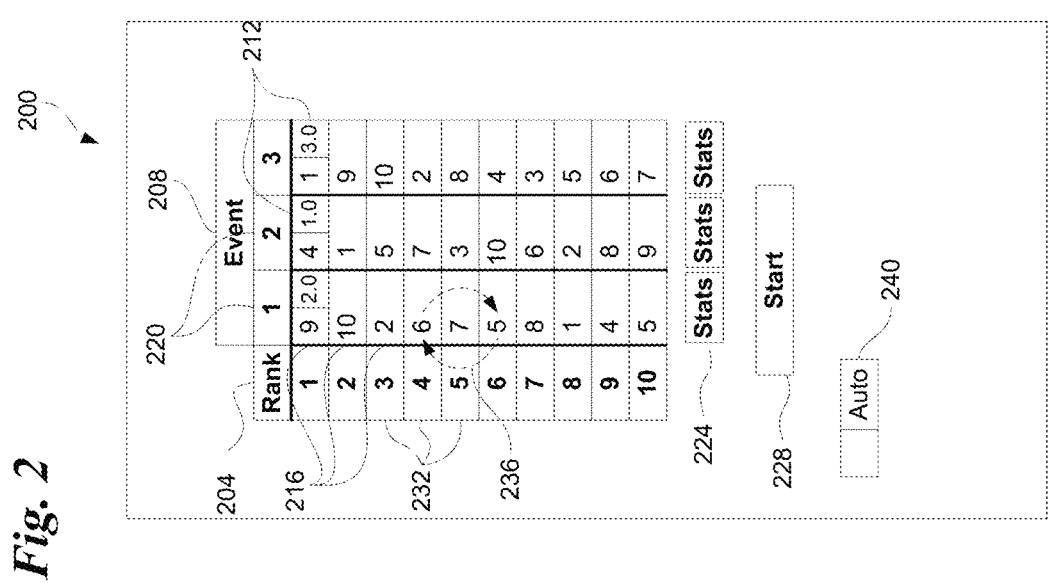

FIG. 2 illustrates at 200 one example of a user interface displaying pre-event or "initial" rankings and configured to accept input from a user specifying a set of predicted rankings by changing the initial rankings supplied by the system for multiple participants participating in an event (see 136 and 112 in FIG. 1). As illustrated, the participants, events, and rankings may be organized in a table 208. Each row 232 in table 208 represents a final ranking 204 (in this case ranking 1 through 10) for each participant 216 in each event. The event is indicated in table 208 as a column 220 which may include internal columns 212.

Internal columns 212 may be optionally included to show the odds of a given participant 216 finishing with given final ranking 204. For example, in FIG. 2, the system indicates that the odds of Participant 9 in Event 1 finishing with a final ranking of 1 (i.e., the highest finishing position) are 2-1. Put another way, the system has determined that before the event took place in the past, the possibility that Participant 9 would achieve that highest rank at the end would merit a return to the bettor of $2 in winnings for every $1 wagered. In a pari-mutuel pool environment, this would mean that a player betting $2 on Participant 9 in Event 1 would receive a payout of $6 ($4 in winnings plus the original stake of $2) if Participant 9 were to achieve the highest finishing position. Similarly, in Event 2, a $2 bet on Participant #4 at odds of 1-1 would return $4 ($2 in winnings plus the original $2 bet) to the player if that participant were to finish in the highest position. In Event 3, a $2 bet on Participant 1 at odds of 3-1 would return $8 ($6 in winnings plus the original $2 bet) to the player if that participant were to finish in the highest position. FIG. 2 illustrates odds in columns 212 for only the highest ranking participants. However, this is only illustrative rather than restrictive as odds may be shown for some, none, or all of the rankings in FIG. 2.

The user interface at 200 may be configured to display table 208 with optional initial rankings calculated by the processor based on the probability of each participant 216 obtaining the highest ranking among all participants for a particular event 220. In another example, the system may provide a user interface like the one shown at 200 where the participants for each event are inserted in the table 208 without reference to any rankings that may have been known before the event took place in the past, or were later calculated by the system. For example, the system may simply enter participants in numerical order leaving it to the user to order them according to the users predicted ranking. Thus the concept of "initial rankings" includes rankings known or calculated in the past before the events took place, rankings computed by processor based on input from a user or data about the participants and events, or an arbitrary ranking of participants provided as a convenience to the user that have no bearing on the expected performance of the participants. In another example, user interface 200 may be initially shown to a user with no rankings (e.g. an empty table 208).

The user may change the initial rankings to match their own predictions. The system may be configured to allow the user to change the rankings by, for example, selecting an individual participant 216 for a particular event using an input device such as a mouse or touchscreen, and then selecting a new position that is different from the original position by, for example dragging the selected participant 216 from the original position to the new position. The system may initially represent participant 5 participating in event 1 with an initial ranking of 4, and an initial ranking of 6 for participant 6. A user may believe that a different outcome is more likely, namely that participant 5 will finish with a ranking of 6, and participant 6 will finish with a ranking of 4.

A user may predict a different outcome than the one initially offered by the system by selecting the cell in table 208 for participant 5 (ranked $4^{th}$) and dragging the cell from its current position to a new position corresponding to a final ranking of 6 as illustrated at 236 in FIG. 2. The system may then automatically swap rankings for participants 5 and 6. The result is thus illustrated in FIG. 2 where the user has changed the initial or pre-event rankings at 236 for participants 5 and 6 rather than accepting the rankings initially presented.

In another example, an event 220 may be represented as a collection of text input fields configured to accept text input from an input device such as a keyboard and/or a mouse. In this example, a user changes the initial rankings to create the predicted rankings by selecting individual participants 216 for a particular event 220 with the mouse, and uses the keyboard to enter the participant 216 the user thinks will finish with the ranking 232 corresponding to the row in table 208.

As illustrated in FIG. 2, the system may initially represent participant 5 participating in event 1 with an initial ranking of 4, and an initial ranking of 6 for participant 6. The user may believe a different outcome is more likely as discussed above. The user can predict this outcome by selecting the text field in the cell for participant 5 (ranked 4th) and entering into the text input field a new participant number, a 6 in this case. The system may then automatically swap participants 5 and 6, or require the user to enter a different participant number for the sixth place ranking. In either case, the result is illustrated in FIG. 2 where the user has changed the initial or pre-event rankings for participants 5 and 6 at 236 rather than accepting the system generated rankings.

As mentioned herein elsewhere, the wagering terminal may accept input from a user by any suitable input device. For example, the wagering terminal may be configured as a "kiosk" or "game console" having a touch screen mounted in the terminal along with a processor, memory, network connection, database access using the network, along with other input and output devices and software configuring the processor to operate as disclosed herein. A keyboard, or pointing device may be included to allow the user to enter data, or the touch screen may include an on-screen keyboard and may be configured to function as both an input device accepting user selections and text and an output device displaying a user interface such as the user interface shown at 200.

A user may wish to consider additional information about the events before deciding on and submitting predicted rankings. Such additional information may be available by selecting one of the buttons 224 which each correspond to one of the events and may provide additional statistical information about the performance of each participant 216. This information may be retrieved from a database (e.g. databases 180, 176, or 172) and may include statistics about a win percentage of participants based on their past experience with various types of venues which in the case of a horse race, may include winning percentages for a particular starting position, track, track surface, and distance. Statistics may also include a win probabilities based on characteristics of people or entities associated with the participants such as trainers, coaches, jockeys, and the performance of the participant in similar events. Regardless of how the rankings are changed by the user, the user may continue to change the ranking for all participants in all events until the user is ready to proceed with submitting the bet and calculating a wager result or score (see FIG. 1 at 140)

This may be done by activating a "start" button 228 on the user interface. Before electing to start, the user may select an "auto" feature at 240. This indicates to the user that the player wishes to accept the pre-event suggested rankings without intervening to change them. With the auto feature activated, the system may hide or minimize user interface 200 allowing the player to bet repeatedly without stopping to review or change the pre-event rankings. An example of this aspect of the process is discussed further below with respect to FIG. 6.

Figure 3:
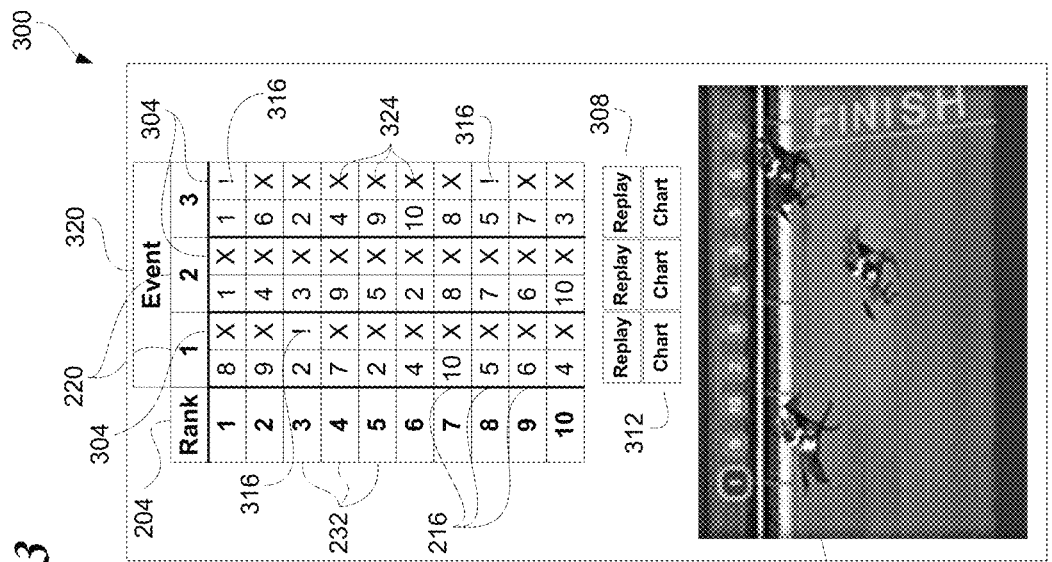
FIGS. 2-4 illustrate various user interface components for presenting output and accepting input according to a method like the method of FIG. 1.

FIG. 3 illustrates 300 as one example of a user interface presenting the wager result calculated at 140 indicating how many of the user's predicted rankings match with the actual final rankings. A scoring table 320 (which may also be characterized as a "score card" or "result") is similar to table 208 and may be displayed (FIG. 1 at 152) by a display device controlled by a processor and configured to generate the user interface at 300. In this example of the user interface, rows 232 represent individual separate rankings 204 as they relate to the participants 216. Columns 220 represent separate events as in table 208, the number of columns 220 corresponds to the number of events the user is making predictions on, and the number of rows 232 represents the number of participants participating in each event.

In one example, columns 220 corresponding to each event may be configured to indicate both the ranking the user selected and the final ranking based on actual results. For each possible ranking for each separate event, column 220 may indicate the user selection (e.g. some indicia identifying the participant such as a number) and a first identifier 316 (here an "!") indicating that the final ranking and predicted ranking match, and a second identifier 324 (here an "X") indicating that the final ranking and predicted ranking do not match.

In the example shown at 300, the user predicted that participant number 2 would finish the first event with a ranking of 3 (e.g. finished in third place in the case of a horse race). In the actual event taking place in the past, participant number 2 did finish with a ranking of 3 and therefore the user's prediction matches the final outcome of the event for participant number 2. A similar result was obtained for participants 1 and 5 in the third event. In this example, none of the user's predicted results match the final actual results for the second event. Although an "X" and an "!" are illustrated as indicating when a user's prediction matches the final actual results, any suitable symbol, graphic, alphanumeric character, and the like may be used. The lack of an indicator may also be used to indicate that the predicted and final results match, or that they do not match. In another example, the second identifier may be a blank space resulting in a display 300 where a figure or some other indicia is used as an identifier indicating when the user's results match the final results with the remaining combinations of event, rank, and participant left blank in the display.

Detailed results may be displayed at 160 when a user selects one of the buttons 308 on user interface 300. Selecting a "replay" button 308 corresponding with an event in one of columns 220 may provide the user with a video or graphical depiction of the event as it actually happened in the past. In the illustrated example, clicking or selecting "replay" 308 opens a video viewer 328 and displays a graphical or recorded result showing each participant (horses in this example) crossing the finish line.

Figure 4:
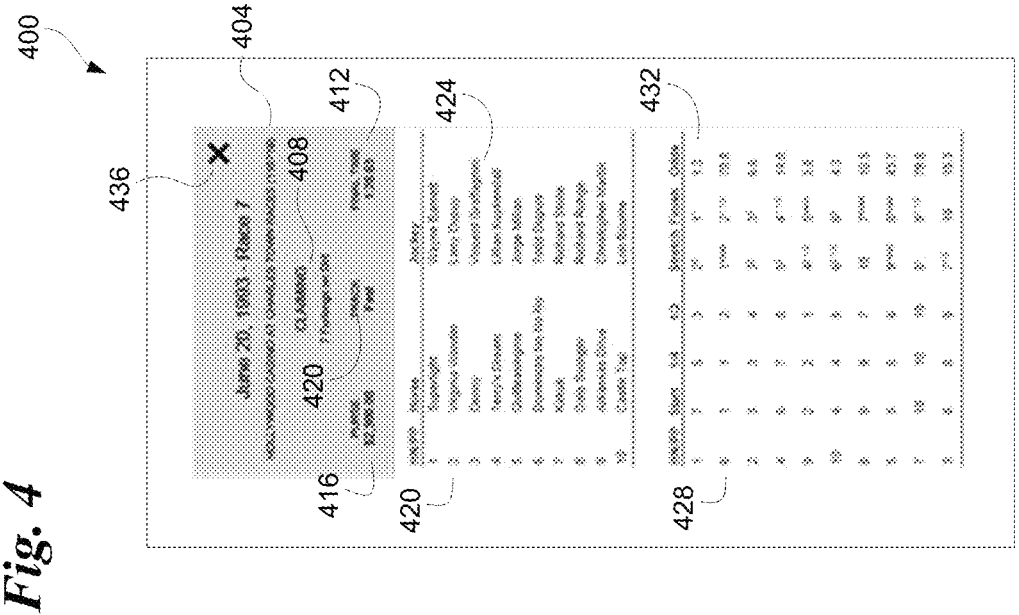

Additional details may also be viewed by clicking or selecting a "chart" button 312. Selecting this option can open a display like the one shown in FIG. 4 at 400 having additional details about the event. One example of the kind of additional details that may be available is shown, although other information may be available in addition to a replay of the event is illustrated in FIG. 4 within the context of a horse race. The date and time of the race, as well as the location are shown at 404, the type of race and race distance at 408, the winning time at 412, and purse at 416. At 420, the name of each horse is shown, and its assigned numerical identifier (e.g. 1-10). The jockey assigned to ride each horse is also listed at 424. Timing information appears at 428 where the arrangement of the horses in the starting gate is shown along with the position of each horse at various points around the track, and at the finish. Winning odds for each horse are also listed at 432. Other information may be displayed as well. For other sports, where the participants are not horses, the information given at 400 may be very different. When the user has finished studying the chart at 400, the chart can be closed by selecting or clicking the "close" icon 436.

Figure 5:
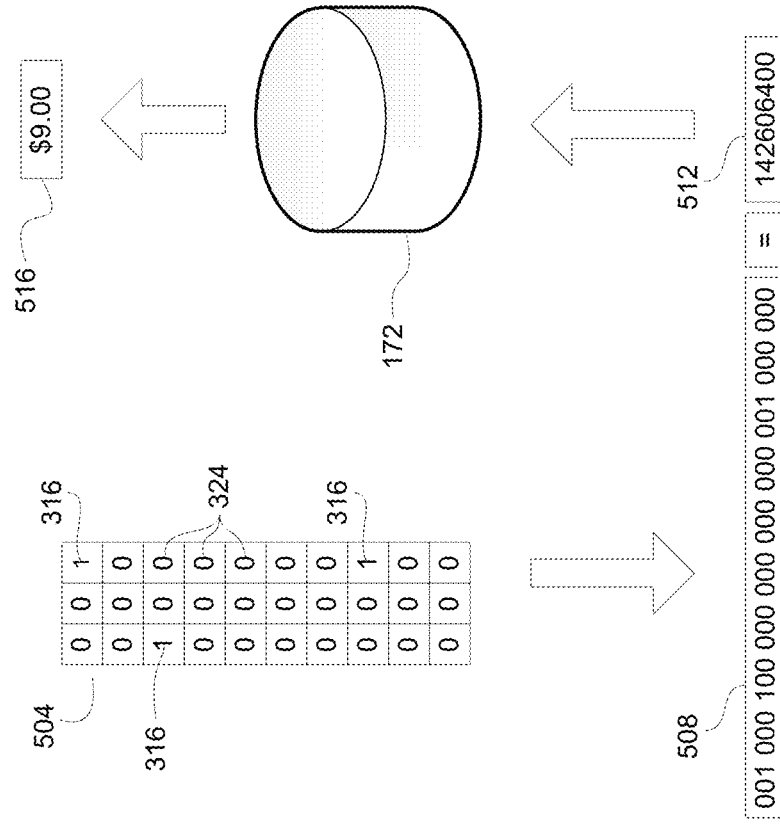
FIG. 5 illustrates aspects of determining the prize amount for a method like the method of FIG. 1.

Below is one example of how the scoring algorithm calculates a wager result or final score at 140. As discussed above with respect to FIGS. 2 and 3, a user predicts the outcome for the participants of multiple historical events individually. Each of the single historical events has a present resulting scorecard shown in FIG. 3 with ten fields for each event, each with two potential states: correctly predicted or incorrectly predicted. A "hit" at 316 indicates a correct prediction, and a miss at 324 indicates an incorrect prediction. An "event pattern" may be created that includes the ordered collection of hits and misses, an example of which is illustrated in FIG. 5 at 504. The event pattern 504 matches the results shown in FIG. 3 where the user only correctly predicted the finishing position for three of the participants. Hits 316 are marked with a "1", while misses 324 are marked with a "0" as shown.

Each potential outcome of a wager that includes the user's predictions can be generated by a processor as a binary number with a number of digits equal to the number of events in the event pattern multiplied by the number of participants in each event. A processor may be configured to assemble a wager result 508 using an algorithm such as Algorithm 1 illustrated in pseudo code below:

---
Algorithm 1
---
```
for each ranking
    for each event
        append hit or miss indicator to
        an alphanumeric string
    done
done
```
---

The results of this example of the procedure appear in FIG. 5, where the wager result 508 is a 30 digit binary number. In the illustrated example, the left-most digit is 1 if the player correctly predicted the highest ranked participant in the first event, and a 0 if not. The second to left-most digit represents whether the user correctly predicted the highest ranked participant of the second event, and so on. For the result 508, the most significant bit is the upper left position in the event pattern (corresponding to the highest ranked participant of the first event), and the least significant bit is the lower right spot (corresponding to the lowest ranked participant of the last event). The wager result 508 may be converted from a base 2 binary representation to a base 10 integer form shown at 512 as 142606400. Either or both of these wager results may be used as disclosed to calculate a prize amount. These wager results (which may also be characterized as "pattern IDs") can range from 0 (where no rankings were predicted correctly in any of the events), to 1,073,741,823 (inclusive) if the user correctly predicts the rankings (pattern) for all 10 participants in all three events.

In this example, there are 2^10 (1,024) possible event patterns like pattern 504 for each event. Some of these patterns that are mathematically possible may be impossible for various reasons. For example, in horse racing, having nine out of the ten horses correctly placed means 9 hits for a 10 position race, and therefore the 10th position must be a hit. In this case, many of the 1024 possible patterns are logically impossible.

For a database (such as database 172, 176, or 180) containing information about, for example, 104,802 events matching the required criteria, some results occur more frequently than others, such as having none of the suggested answers correct (19,423 times out of 104,802) or all of them correct (1 out of 104,802). If three events are considered, a final scorecard or event pattern will have patterns for each of the three races. Therefore, considering the case where there are 862 possible patterns for each event, an event pattern 504 with 862 possibilities per event yields an event pattern with (640,503,928) patterns with a non-zero probability of occurrence (assuming users always accept the initial rankings recommended by the system). For each of these patterns the probability of it occurring can be calculated by multiplying the probabilities of the event patterns for each event. Wager results can be assigned a probability based on their odds as represented in the actual data about the events assuming the user accepts the initial rankings calculated by the system (calculated at 132 in FIG. 1). Based on this assumption, approximately half of the approximately 1.073 trillion wager results have a zero probability. These patterns can only be achieved if a player modifies the recommended finishing order.

These probabilities can be used by the system in calculating or determining prizes (156 in FIG. 1). In one example, ranges of possible outcomes represented using the wager results (like the number 142606400 mentioned in the example above) as a key or identifier for a database query where wager results are assigned to prizes. This assignment may include other criteria allowing prizes for the same wager result to be different for different math models, denominations, bet levels, and take out percentages. Manufacturers may implement these various criteria as records in a database, or entries in a file such as a Math Definition File (MDF) provided for each math model.

In one example, for wager results (i.e. pattern IDs) 0 to 300,000,000, the processor may be programmed to assign a prize value of zero for a particular math model if the sum of the probabilities of those results equals the probability defined in the MDF for prize 0. The processor may be programmed to assign a prize value of 2 for results in the range of 300,000,001 to 400,500,000 if the sum of the probabilities matches the prize frequencies defined in the MDF for prize 2, and so forth.

To assign prize ranges to an MDF file, the most valuable prize may be mapped first beginning with the highest possible pattern ID (1,073,741,823) and adding pattern ID probabilities while counting down by 1 until the probability of the top prize is exceeded. At this point the pattern ID is recorded as the lower bound for the top prize and the maximum pattern ID is recorded as the upper bound for the top prize. This process is repeated while stepping down through the pattern IDs until every prize in the MDF is accounted for including the 0 prize receiving all remaining pattern IDs down to 0.

For each math model, bet level, and payout percentage combination, a table may be generated by a processor (e.g. in computer separate from the wagering terminal) using this method with three columns: Low Index, High Index, and Prize Index. In this example, the Prize Index may identify the prize to be awarded and the Low Index (inclusive) and High Index (inclusive) may represent the upper and lower ends of the pattern ID range assigned to the Prize Index. As noted, these pattern ID tables may be generated "offline" prior to deployment of each theme, bet level, and payout percentage combination based on the specific mathematical probabilities specified in the database (such as database 172 in FIG. 1).

Probabilities and pattern ID ranges may require recalculation if the event database is replaced. Using this kind of algorithm, the processor may generate prize tables with the probability of a pattern ID in a particular range that is as close as possible to the theme designer's desired probability for a given prize, and it assumes that the players accept the initial rankings recommended at the outset. The actual prizes paid out may deviate from the design if players do not play optimally.

With the database preloaded with the proper prizes for all possible combinations of math model, bet level, and payout percentage, the system can quickly calculate the wager results and query the database to look up the prize to award based on the user's resulting pattern ID regardless of whether the player has modified the initial rankings or not. Once the prize amount 516 is calculated at 156, the prize amount can be displayed on the display device for the wagering terminal.

As illustrated in FIGS. 2-4, betting on multiple past events may provide an entertaining theme without spinning reels or any other casino style gaming mechanism. A display device displaying the elements illustrated in FIGS. 2-4 can be used to order the outcome of multiple events. The theme may include accompanying depictions and animated highlights of matching predictions as the participants complete the event. Similar to bingo, the system may display the matches with graphics, symbols, and other indicia particular to the type of event.

Figure 6:
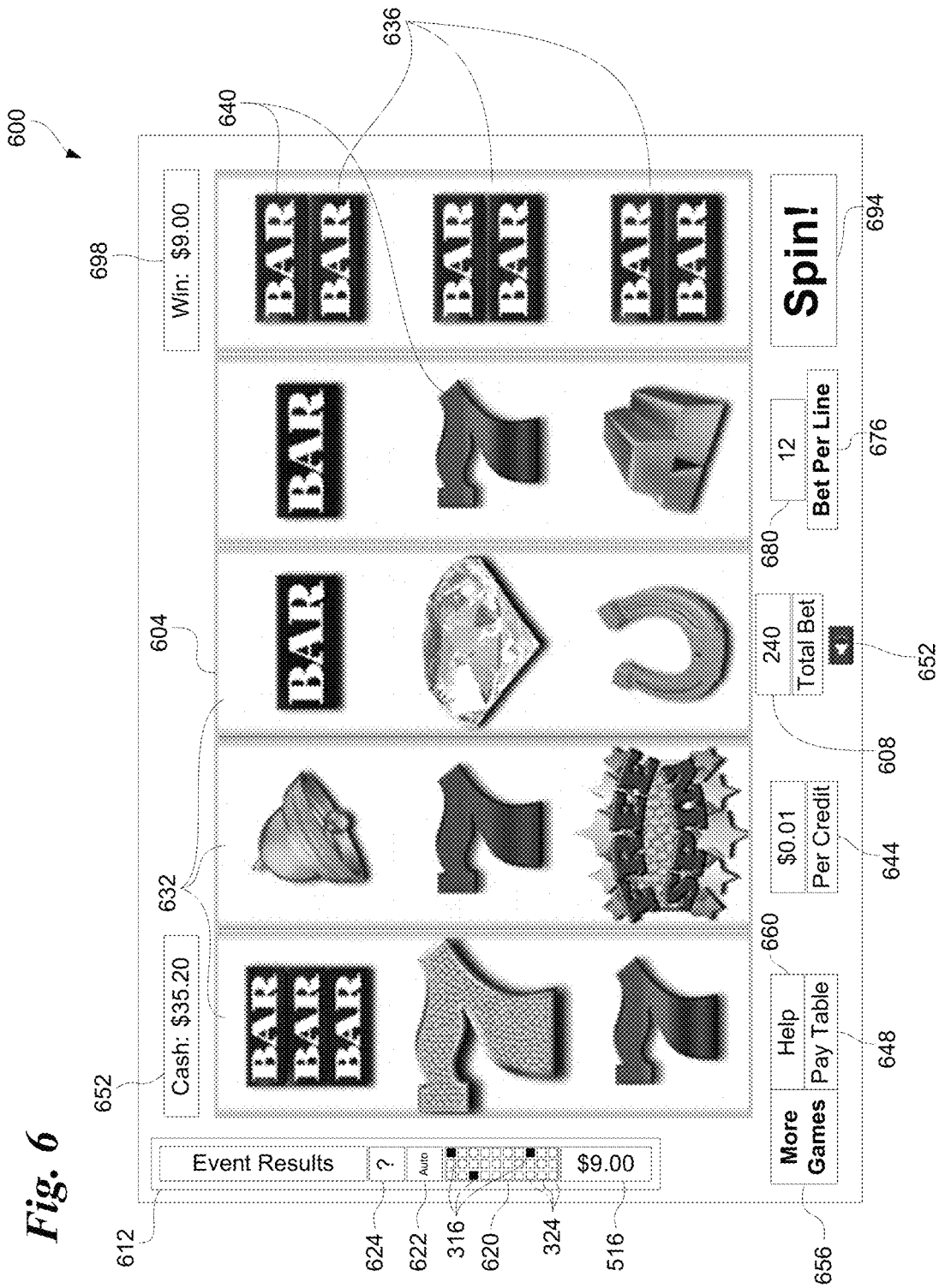
FIG. 6 illustrates another user interface for presenting output and accepting input according to a method like the method of FIG. 1.

Wagering on multiple past events as discussed herein may also be integrated into any suitable flow or sequence of actions and may be included with other actions taken by a user in the context of a larger overall theme. As discussed previously, such a theme may optionally be selected at 104 (see FIG. 1) early in the wagering process. One example of a theme generated by the processor in an electronic wagering device is illustrated in FIG. 6 at 600. In this example, the terminal is configured to allow users to wager on multiple past events by including other graphics, colors, symbols, and various indicia to enhance the overall user experience.

For example, in FIG. 6, the user interface includes a thematic display 604 and a minimized or miniaturized event selection interface 612 which can expand across the user interface to include a user interface like user interface 200. Such a user interface may be configured to accept input from the user to change predictions as discussed herein elsewhere. User interface 612 may also be configured like user interface 300 where the processor is configured to generate a suitable arrangement of indicia appearing on user interface 612 for indicating the results of the user's predictions. A minimized or miniature score table 620 may also be included interface 612 and configured to display a graphical expression of similarities between the user's predictions, and the actual results of the past events. This graphical expression of the results may appear like the event pattern 504 in FIG. 5 where hits 316 may be represented as filled in boxes, while misses 324 may be represented as empty boxes. The prize amount calculated based on the selected theme, wager result, bet level, and other factors discussed above is shown at 516. As shown, the user has selected the "auto" feature 622 which allows the user to bet based on the pre-event rankings provided by the system automatically.

In this example display at 600, the theme includes an array of symbols 640 arranged in a grid or table with a number of columns 632 (here shown as five columns), where each column includes a number of rows 636 of symbols 640 (here shown as three rows). The type, arrangement, or animation of symbols 640 may indicate a winning or losing bet. For example, the selected theme may indicate a winning bet by placing symbols 640 in certain preprogrammed alignments indicating a winning or losing bet. Any suitable alignment, or number of suitable alignments of symbols 640 in columns 632 and rows 636, may be configured to appear based on the results of the user's predictions as discussed elsewhere. Such alignments may be preprogrammed to correspond to the various wager results (such as wager results 140 and 508). For example, when a user has placed a winning bet, the processor may be configured to display additional lines between symbols 640, to display flashing, blinking, or otherwise animated symbols 640, and/or to optionally generate audible music or other sounds. Theme 600 may include any suitable combination of graphical, audible, or other elements indicating a winning or losing wager. Audible features, such as the volume or type of sounds generated by the electronic wagering terminal may be controlled by an audio element 652.

Control and informational elements, data entry fields, and buttons may be included in user interface 600 and may be configured to accept input from the user. Available cash to wager may be shown at 652, and any winnings received as a result of the predictions on past events made by the user may appear at 698. A "help" panel may be included at 660 explaining aspects such as how to select rankings for the multiple participants of past events, the process of making wagers, and how winning and losing bets are indicated, to name a few. A pay table element 648 may be included providing any suitable explanations to the user as to how a particular wager will pay out, and may include an explanation of any corresponding arrangements of symbols 640 that may be shown. Control elements may also be included in interface 600 such as fields for entering, selecting, or simply displaying the number of dollars per "credit" at 644. A user may bet according to the number of winning configurations of symbols configured for a given theme and displayed by the processor. A bet per winning configuration (here shown as a number of credits) may be optionally entered or selected at 680 and may be confirmed with a button 676. The wager may be placed by selecting the "spin" button 694.

As noted above, display 600 includes various symbols 640, and other features that may be displayed by the processor according to whether the user has made a winning prediction on the results of the past events. As discussed herein elsewhere, the final scorecard or event pattern is used to calculate the actual payout, for example, by calculating a pattern ID and using the pattern ID to determine the prize amount based on the math model, bet level, pay percentages, and other aspects discussed above. Based on the user's predictions, and the final results, the processor may execute logic programmed in a prize selection module to select a configuration of symbols 640 and any other corresponding user interface elements to indicate a winning wager results.

As noted above with respect to FIG. 2, if the user selects the "auto" feature, indicated at 622, the user can place bets repeatedly relying on the pre-event rankings automatically calculated using the processor without expanding event selection interface 612 to display all the options illustrated in FIGS. 2 and 3. In this example, the user can repeatedly place bets, and view the results without making changes to the predicted rankings. A user can repeatedly make bets using the control elements featured in the user interface at 600 to operate the system in a familiar way except that as disclosed herein, the prize amounts paid out to bettors are not based on randomly appearing configurations of symbols 640 or a random number generator, but on the difference between the predicted and actual results of multiple past events. This is in contrast to many casino wagering terminals where a bettor is betting on the occurrence of various winning configurations of randomly positioned symbols 640.

Figure 7:
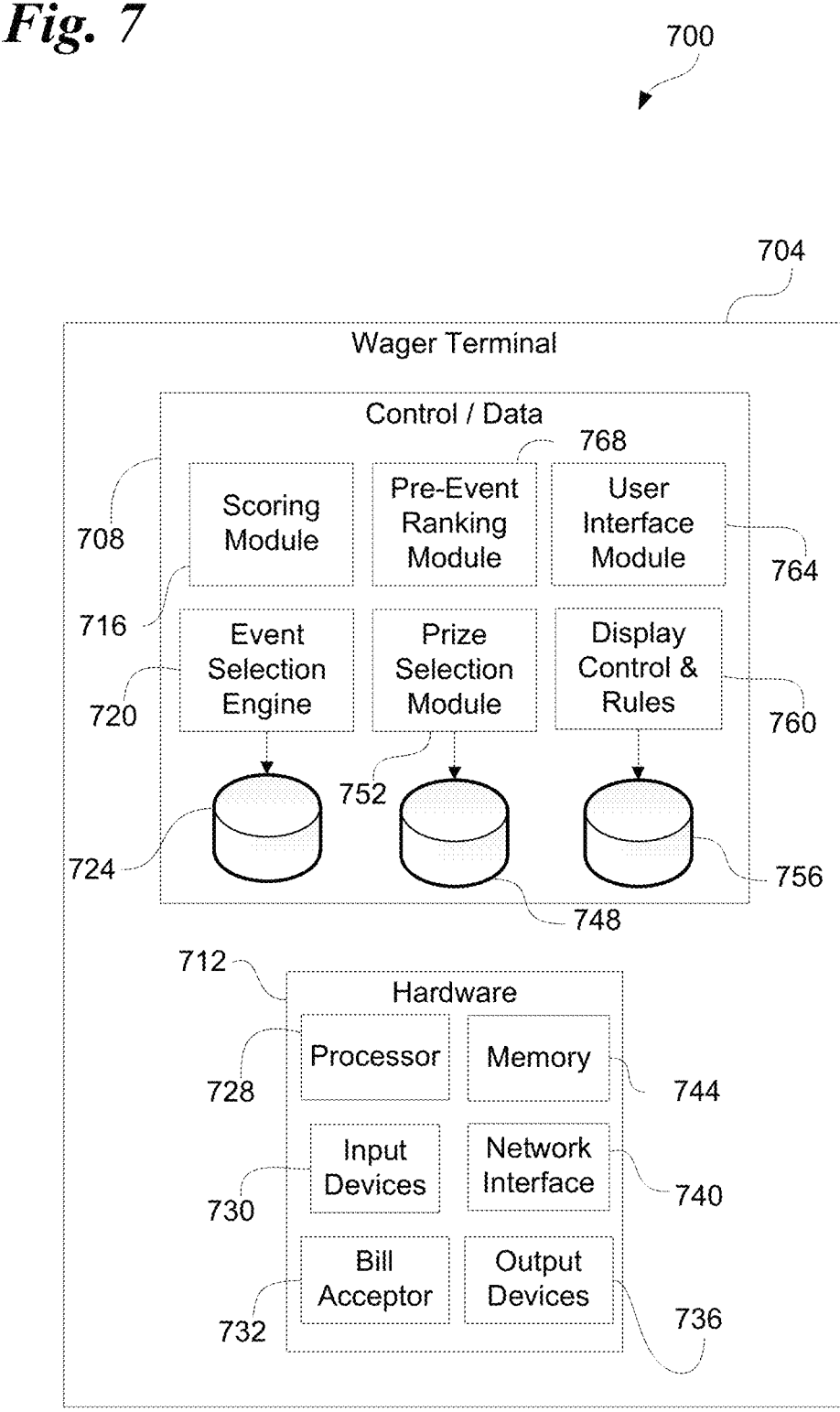
FIG. 7 illustrates a block diagram of one example of a system for performing aspects of a method like the method of claim 1.
Figure 8:
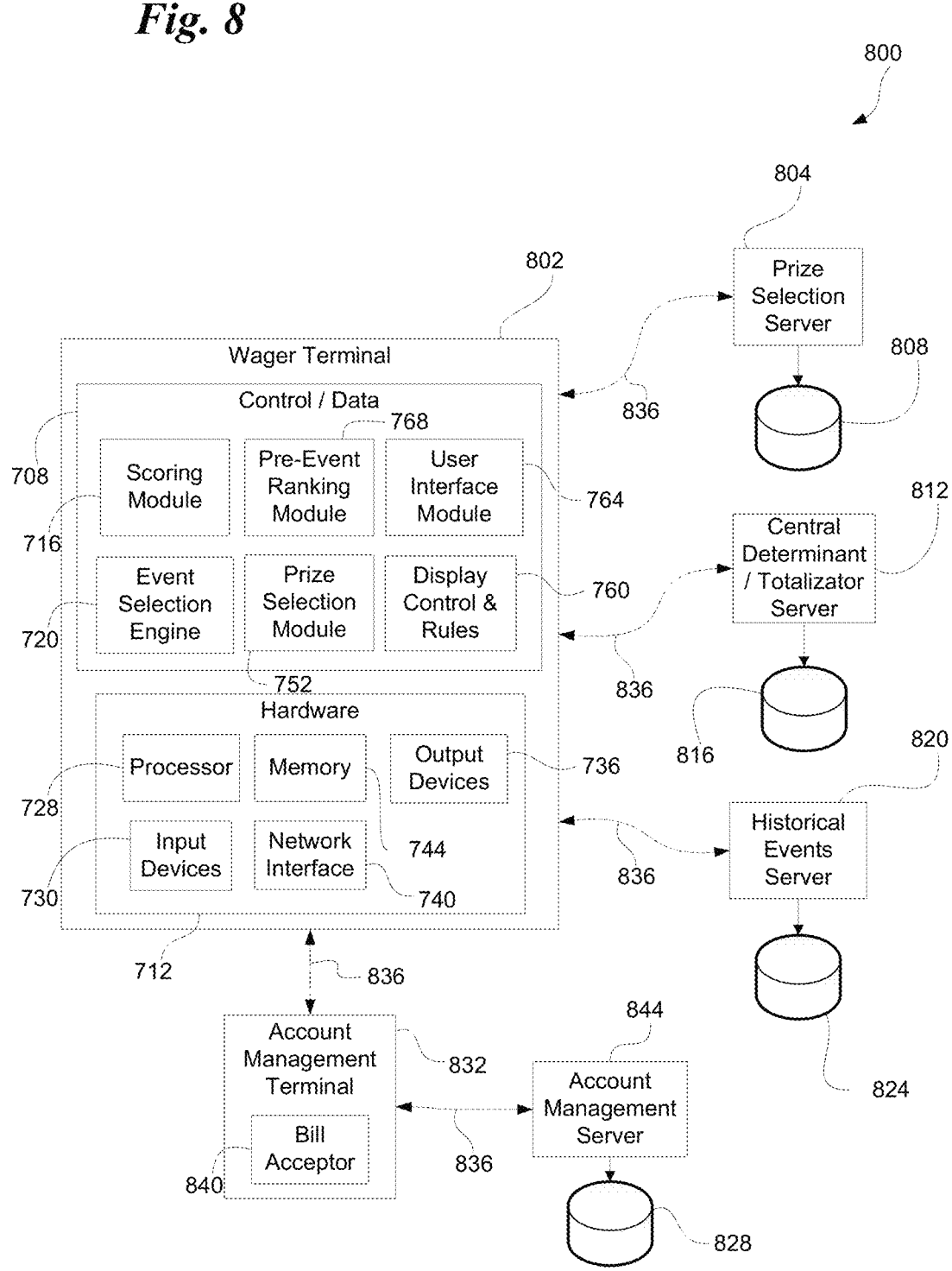
FIG. 8 illustrates a block diagram of another example of the system of claim 7.

FIG. 7 illustrates at 700 one example of the system components that may be included in a wagering terminal to operate the disclosed gaming system. Wagering terminal 704 optionally includes various hardware components 712 that may include a processor 728, memory 744, network interface 740 which may be used to access database(s) such as event database 724, prize database 748, and display control and rules database 756 which may contain data about the sequence of play, screens to display at various points in the process, common prize pools, and available themes and associated rules to load and execute using processor 728. In on example, the common prize pool may be maintained in database 756 which may be part of a totalizator device, or part of a system configured to operate as a totalizator.

Wagering terminal 704 may include one or more output devices 736, one or more input devices 730, and also an optional bill acceptor 732.

The terminal 704 may also include various software and data components 708 that may be used by the processor as disclosed herein. Software 708 may include a scoring module 716 configured to calculate a final score based on the difference between the user selected rankings for the participants of the multiple events and final rankings of the participants ranked according to the actual results of the events that occurred in the past.

A pre-event ranking module 768 may be included and configured to calculate an initial ranking for each participant calculated using the odds of each respective participant completing the event with the highest final ranking as determined in the past before the event took place. The data about the multiple events may be retrieved from a database such as event database 724 which may be similar to database 176 and may include data about the multiple events, and about the participants competing in those events. Like database 176, database 724 may include race replay information such as video clips, or graphical representations of the results of various events. It may also include charts, graphs, statistical data, and the like explaining predicted results and actual final results for various participants participating in past events.

A user interface module 764 may be included and configured to control a display device or other suitable output device 736 to display the initial rankings using the processor. The user interface module may also be configured to accept user input defining user selected rankings, wherein the user selected rankings are defined by changing the initial rankings for at least one participant for at least one of the selected events using an input device 730.

The terminal software 708 may include an event selection engine 720 configured to use the processor 728 to retrieve event data about multiple selected events that occurred in the past from the database. This event data may include data about multiple participants participating in the selected events retrieved from event database 724.

Software 708 may include a scoring module 716 configured to calculate a final score as disclosed herein based on the difference between the user selected rankings for the participants and final rankings of the participants using the processor. The final rankings may be ranked according to the actual results of the event that occurred in the past.

A prize selection module may also be included and configured to calculate the prize amount using the processor. The prize amount may be a currency amount based on the final score and the amount to be wagered by the user.

In the terminal at 700, a display and control module 760 may be included and configured to use the processor to initiate a transfer of an amount to be wagered into a common prize pool, and to use the processor to initiate a transfer of a prize amount out of the common prize pool when the prize amount is greater than zero.

Databases 724, 748, and 756 are described herein separately as maintaining different data. Database 724, 748, and 756 may be configured to store the separate data in a single "database" as defined herein with a single organized collection of information maintaining the data discussed. Databases 724, 748, and 756 may be configured as individual collections of data maintained by separate Database Management Systems (DBMS), or as a single collection of data separated logically and maintained by a single DBMS. Whether separate databases, or a single database with various types of data stored therein, databases 724, 748, and 756

(and any other databases used by terminal 704) may be maintained within a single physical server or within multiple physical servers communicating via a computer network. Any or all of these sevvers could be included as part of terminal 704 or separate from it.

The databases used by terminal 704 may also be physically stored on a single storage media such as a Hard Disc Drive (HDD) mounted in terminal 704, or on any combination of separate individual storage media in terminal 704. In another example, the media may be stored on other servers in any suitable configuration accessible by terminal 704.

Terminal 802 is one example of a terminal that communicates with database servers that may not be located in the terminal, but may be available at remote locations from terminal 802 via a computer network 836, or multiple computer networks 836 as illustrated. The computer network(s) 836 may communicate via network interface 740 to pass information to the processor 728 and other hardware 712, as well as control and data components 708.

For example, an account management terminal 832 may be separate from terminal 802 and may be configured to communicate with terminal 802 via network 836. The account manager terminal 832 may include a bill acceptor 840 configured to scan and accept currency. Account management terminal 832 may also include devices for creating or accepting, vouchers, credit cards, and the like, allowing the customer to add money to their account and prepare to make bets. Account management terminal 832 may also include a processor, memory, input devices, output devices, and a network interface as illustrated with wagering terminal 802. Various software or other control modules may also be included to manage the collection and payment of wagers and prizes to the user's account. These amounts added and removed from a user's account, and the transactions associated with them, may be maintained in an account management database 828 accessible via an account management server 844.

In another example, a prize selection server 804 may access a prize database 808 like prize database 172 and 748. Terminal 802 may access prize selection server 804 using a network such as network 836 via network interface 740. Prize selection server 804 may be configured to map winning scores calculated by prize selection module 752 to determine prize amounts with respect to wager results, pattern IDs, and price ranges as discussed above with respect to FIG. 5. Prize selection module 752 may access prize selection server 804 and prize database 808 using any suitable procedure to arrive at prize payouts where the user has successfully matched predicted results with actual results of past events.

Wagering terminal 802 may also include display control module 768 which may be configured to access central determinant/totalizator server 812 using network 836 via network interface 740. Server 812 may be configured to access the database 816 which may be similar to database 756, or any of databases 180, 176, or 172 in FIG. 1 and may include math models, themes, and other control or rule related data. Similarly, event selection engine 720 may access a historical event server 820 using network 836 and network interface 740. Display control and rules module 760 may access server 812 as needed to display output and determine what input to accept according to math model definitions retrieved from database 816. In another example, display server 812 may also be configured to provide software upgrades to display control and rules module 760. It may also be configured to upload graphics, templates, screen positioning information, display control logic, and the like by any suitable means such as a firmware upgrade, or other software upgrade.

Historical event server 820 may be configured to access a historical events database 824 which may be like events database 724 or database 176. Historical events database 824 may include race replay information such as data about participants and events, including odds, associated parties to members, and the like and video clips, or graphical representations of the results of various events. It may also include charts, graphs, statistical data, and the like explaining predicted results and actual final results for the participants in the events themselves.

As illustrated at 800, wager terminal 802 may include within the terminal itself a limited capacity for storage of the various process control, prize, account management, and event data storage components. In this configuration, the wager terminal may provide the functionality discussed herein while relying on a network like network 836 to access themes, math models, event information, prize selection information, and account management data. This configuration facilitates a distributed processing arrangement where wager terminals may be implemented in software operating on a personal computing device coupled to network 836. Network 836 may be a wireless or wired network accessible within a certain location or venue where the opportunity to participate in wagering on past events is restricted to a specific geographical area by limiting the extent of the range of accessibility to network 836. Electronic wagering devices (wagering terminals) inside the range of network 836 may be used to participate in the wagering, while wagering devices outside the range of network 836 may not be able to participate until the wagering terminals move within the range of network 836. Mobile wagering terminals include personal computing devices programmed or otherwise configured to perform the wagering procedures disclosed herein.

One example of a mobile wagering terminal limited by the range of network 836 is a personal computing device such as a smart phone with processor, memory, input/output devices, display device, etc. configured to execute a wagering application. The application may be programmed to perform some or all of the disclosed wagering processes by remotely accessing databases like 808, 816, 824, and/or 828 via servers 804, 812, 820, and/or 844 respectively. When the mobile device is inside a predetermined area of network coverage for network 836, wagering may proceed as discussed herein. When the user carries the device outside the coverage of network 836, access to the data may be lost and the wagering process suspended until the user reenters the coverage area of network 836. This coverage area may be implemented by wired or wireless access points providing a physical and/or electronic connection to network 836.

In another example, multiple wager terminals 802 may be configured to operate on a general-purpose computer placed in a particular venue or facility for use by the general public. In this example, rules, prize information, scoring, and the like may be available through network 836 making the wager terminals 802 in this configuration easier to maintain, and upgrade. In another example, a wager terminal may be a hybrid of terminal 802, and terminal 704 where the terminal may have access to various remote databases and servers for managing the wagering process as discussed above with terminal 802, but may cash or store some or all of the data and control logic in an internal database as well. This configuration may thus provide higher perceived performance for the user because of reduced time lag that may be caused by repeated network access.

Figure 9:
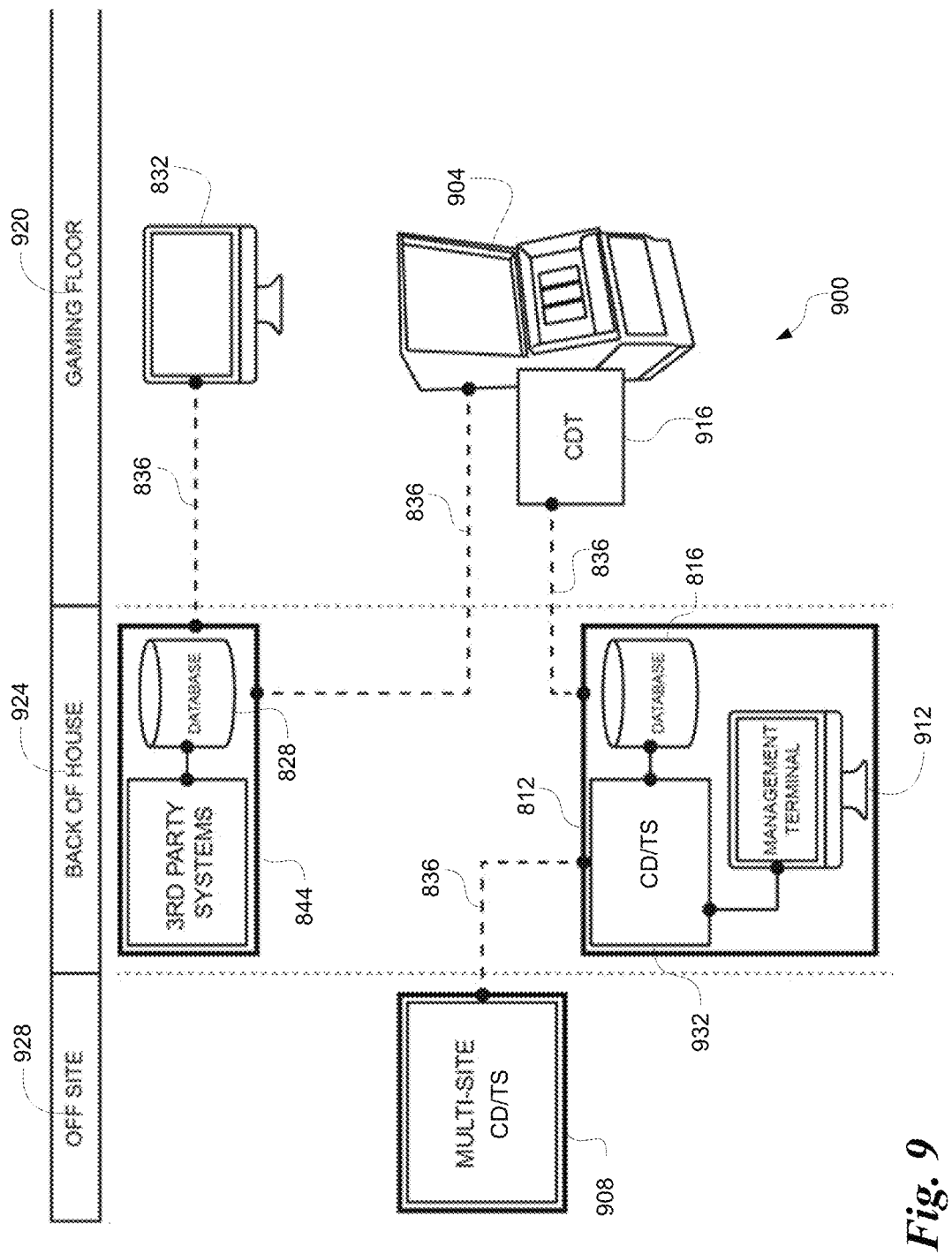
FIG. 9 illustrates a block diagram of another example of the system of claim 7.

Illustrated at 900 in FIG. 9 is another example of the system disclosed herein similar to the system discussed above at 800 illustrating aspects of how the various components disclosed herein may be integrated into a gaming venue. Account management terminal 832 may access an account management server 844 which includes an account management database 828. This access may be facilitated by a network 836 as discussed above. The wager terminal 904 that may be configured like terminal 804 may include a Central Determinate Translator (CDT) module 916 as illustrated. Wager terminal 904 may be positioned along with account management terminal 832 on the gaming floor 920 of a gaming venue. Gaming floor 920 may be the area accessible to users of the gaming system described herein. Wagering terminal 904 may be an immobile configured to remain stationary as the user interacts with it. Wagering terminal 904 may also be a personal computing device.

One or more wagering terminals 904 may communicate via network 836 to server 812 which may include event database 816 and a Central Determinate/Translator System (CD/TS) 932. Server 812 may also include a management terminal 912 allowing system managers to maintain rules, information about past events, math model definitions, and any other logic or data used by the system as discussed herein elsewhere. Server 812, CD/TS 932, and management terminal 912 may be positioned in a "back of house" area 924 of a venue available to administrative or other employees of the venue. This area may also include account management server 844 account management database 828. Server 844 and 812 may be maintained in a separate location within a venue or in a separate location remote from the venue accessible to terminals 904 and 832 via network 836.

Terminal 904 may include a CDT module 916 communicating with CD/TS servers 932 and 908. The CDTS servers and module 916 may be configured to provide gaming infrastructure that both simplifies operations for the gaming facility and simplifies development for gaming equipment manufacturers. In some cases, a software emulator of the CDT hardware may be incorporated in terminal 904, or other components. The CDT functionality may be included with the CDTS and deployed in a variety of server and software configurations to meet various jurisdictional requirements. These configurations can include Class II Bingo, Virtual Scratch Tickets, Historical Racing, Racing Based Gaming and variants that utilize previously run races to generate outcomes, and/or other forms of central determinate gaming.

As illustrated in FIG. 9, wagering terminals may include a cabinet, computer, display, input/output devices, and other peripherals. The computer may be programmed with software configured to carry out the methods and processes disclosed herein, and may optionally be programmed to perform other processes as well. Unlike traditional wagering terminals that include an internal random prize generator, a terminal 904 may include a central determinate gaming logic or equipment programmed to receive prize outcomes from an external device or system. The CDT aware servers 812 and 844, and others, can cooperate to manage account balances, communicates with the system, display user interface screens or other information, and display outcomes calculated by the system in an entertaining way. This may be done using a variety of add on components available to system operators to enhance manageability and guest experience. These include accounting systems and player rewards systems. These systems may connect to wagering terminals such as terminal 904 directly or through a server such as server 812 using a network like network 836 depending on the specific capabilities of the systems and devices provided by various vendors.

The CD/TS 908 and/or 912 may provide access to additional math models increasing the number and quality of themes available to smaller venues by accessing a central server like server 908, either directly or via another server on-site such as server 812. Modifications to servers 844, 812, and 908 necessary to add additional wagering terminals 904 are reduced increasing opportunities for different types of terminals from various manufacturers. Such terminals may include terminals implemented in software and operated on a personal computing device.

The disclosed system may use CDT architecture to provide outcomes to wagering terminals based on a pari-mutuel wagering system using historical events such as horse races, dog races, auto races, and any other suitable event. As discussed herein, users may place wagers attempting to predict the finishing order of events assisted by the display of pre-event odds or other handicapping information. Users may enjoy a variety of diverse, entertaining prize displays (such as the display at 600) based on successfully predicting event outcomes.

Using the CDTS configuration illustrated at 900 allows a generic outcome delivery protocol (the CDT Protocol) allowing diverse wagering terminals to request outcomes from a central determinant system in a universal format. Similarly, a CDT may be installed in each wagering terminal as a physical piece of hardware, a software module, or as a game integrated display capable of displaying jurisdiction specific information and player interface elements. A combination of the standardized protocol and/or display components may separate the wagering terminal itself from the outcome generation system. Therefore, the outcome generation system can change without corresponding changes on the wagering terminal. The CD/TS can provide central determinant outcomes and the interfaces/displays related to them to the wagering terminal. The wagering terminal can provide an entertaining display of the result and other functions including accounting, player tracking, and general regulatory compliance. Operators can choose a terminal 904 manufactured from a wide array of sources with different functions. Terminals integrated with access to a CD/TS server may also coexist on a floor with non-CD/TS terminals and devices.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

Glossary of Definitions and Alternatives

The language used in the claims and specification is to only have its plain and ordinary meaning, except as explicitly defined below. The words in these definitions are to only have their plain and ordinary meaning. Such plain and ordinary meaning is inclusive of all consistent dictionary definitions from the most recently published Webster's and Random House dictionaries. As used in the specification and claims, the following definitions apply to the following terms or common variations thereof (e.g., singular/plural forms, past/present tenses, etc.):

"Bill acceptor", "currency detector", or "currency validator" generally refers to any device configured to automatically scan paper or metal currency to determine the denominations scanned as well as whether the currency is genuine or counterfeit. Such devices are generally configured and programmed to perform various tests, to determine if the nominations of the currency and whether or not it is counterfeit. In operation, if the bill or coin is considered genuine, it is accepted and retained within the machine and its amount calculated. If the bill or coin deemed counterfeit or otherwise rejected by the machine, it is generally returned to the customer by dropping the currency into a receptacle for retrieval, or by injecting the currency from a slot or opening within which it was initially placed for examination. Various techniques may be employed for sensing whether currency is counterfeit such as magnetic or optical sensing for various physical or other properties of the currency such as weight, size, response to ultraviolet light, and/or the shape or position of particular patterns printed or imprinted in the currency.

"Computer" generally refers to any computing device configured to compute a result from any number of input values or variables. A computer may include a processor for performing calculations to process input or output. A computer may include a memory for storing values to be processed by the processor, or for storing the results of previous processing.

A computer may also be configured to accept input and output from a wide array of input and output devices for receiving or sending values. Such devices include other computers, keyboards, mice, visual displays, printers, industrial equipment, and systems or machinery of all types and sizes. For example, a computer can control a network interface to perform various network communications upon request. The network interface may be part of the computer, or characterized as separate and remote from the computer.

A computer may be a single, physical, computing device such as a desktop computer, a laptop computer, or may be composed of multiple devices of the same type such as a group of servers operating as one device in a networked cluster, or a heterogeneous combination of different computing devices operating as one computer and linked together by a communication network. The communication network connected to the computer may also be connected to a wider network such as the internet. Thus computer may include one or more physical processors or other computing devices or circuitry, and may also include any suitable type of memory.

A computer may also be a virtual computing platform having an unknown or fluctuating number of physical processors and memories or memory devices. A computer may thus be physically located in one geographical location or physically spread across several widely scattered locations with multiple processors linked together by a communication network to operate as a single computer.

The concept of "computer" and "processor" within a computer or computing device also encompasses any such processor or computing device serving to make calculations or comparisons as part of disclosed system. Processing operations related to threshold comparisons, rules comparisons, calculations, and the like occurring in a computer may occur, for example, on separate servers, the same server with separate processors, or on a virtual computing environment having an unknown number of physical processors as described above.

A computer may be optionally coupled to one or more visual displays and/or may include an integrated visual display. Likewise, displays may be of the same type, or a heterogeneous combination of different visual devices. A computer may also include one or more operator input devices such as a keyboard, mouse, touch screen, laser or infrared pointing device, or gyroscopic pointing device to name just a few representative examples. Also, besides a display, one or more other output devices may be included such as a printer, plotter, industrial manufacturing machine, 3D printer, and the like. As such, various display, input and output device arrangements are possible.

Multiple computers or computing devices may be configured to communicate with one another or with other devices over wired or wireless communication links to form a network. Network communications may pass through various computers operating as network appliances such as switches, routers, firewalls or other network devices or interfaces before passing over other larger computer networks such as the internet. Communications can also be passed over the network as wireless data transmissions carried over electromagnetic waves through transmission lines or free space. Such communications include using WiFi or other Wireless Local Area Network (WLAN) or a cellular transmitter/receiver to transfer data. Such signals conform to any of a number of wireless or mobile telecommunications technology standards such as 802.11a/b/g/n, 3G, 4G, and the like.

"Data" generally refers to one or more values of qualitative or quantitative variables that are usually the result of measurements. Data may be considered "atomic" as being finite individual units of specific information. Data can also be thought of as a value or set of values that includes a frame of reference indicating some meaning associated with the values. For example, the number "2" alone is a symbol that absent some context is meaningless. The number "2" may be considered "data" when it is understood to indicate the finishing position of a particular horse in a horse race.

Data may be organized and represented in a structured format. Examples include a tabular representation using rows and columns, a tree representation with a set of nodes considered to have a parent-children relationship, or a graph representation as a set of connected nodes to name a few.

The term "data" can refer to unprocessed data or "raw data" such as a collection of numbers, characters, or other symbols representing individual facts or opinions. Data may be collected by sensors in controlled or uncontrolled environments, or generated by observation, recording, or by processing of other data. The word "data" may be used in a plural or singular form. The older plural form "datum" may be used as well.

"Database" or "data store" generally refers to an organized collection of data. The data is typically organized to model aspects of the real world in a way that supports processes obtaining information about the world from the data. Access to the data is generally provided by a "Database Management System" (DBMS) consisting of an individual computer software program or organized set of software programs that allow user to interact with one or more databases providing access to data stored in the database (although user access restrictions may be put in place to limit access to some portion of the data). The DBMS provides various functions that allow entry, storage and retrieval of large quantities of information as well as ways to manage how that information is organized. A database is not generally portable across different DBMSs, but different DBMSs can interoperate by using standardized protocols and languages such as Structured Query Language (SQL), Open Database Connectivity (ODBC), Java Database Connectivity (JDBC), or Extensible Markup Language (XML) to allow a single application to work with more than one DBMS.

Databases and their corresponding database management systems are often classified according to a particular database model they support. Examples include a DBMS that relies on the "relational model" for storing data, usually referred to as Relational Database Management Systems (RDBMS). Such systems commonly use some variation of SQL to perform functions which include querying, formatting, administering, and updating an RDBMS. Other examples of database models include the "object" model, the "object-relational" model, the "file", "indexed file" or "flat-file" models, the "hierarchical" model, the "network" model, the "document" model, the "XML" model using some variation of XML, the "entity-attribute-value" model, and others.

Examples of commercially available database management systems include PostgreSQL provided by the PostgreSQL Global Development Group; Microsoft SQL Server provided by the Microsoft Corporation of Redmond, Wash., USA; MySQL and various versions of the Oracle DBMS, often referred to as simply "Oracle" both separately offered by the Oracle Corporation of Redwood City, Calif., USA; the DBMS generally referred to as "SAP" provided by SAP SE of Walldorf, Germany; and the DB2 DBMS provided by the International Business Machines Corporation (IBM) of Armonk, N.Y., USA.

The database and the DBMS software may also be referred to collectively as a "database". Similarly, the term "database" may also collectively refer to the database, the corresponding DBMS software, and a physical computer or collection of computers. Thus the term "database" may refer to the data, software for managing the data, and/or a physical computer that includes some or all of the data and/or the software for managing the data.

"Coupled entry" generally refers to two or more horses owned or trained by the same person or entity that are in the starting field for the same horse race and are grouped together for wagering purposes.

"Dead heat" generally refers to a tie between final rankings for two or more participants in an event such as a sporting event. For example, a "dead heat" in horse racing is where two or more horses tie for a "win" or "placing" (first or second place).

"Display device" generally refers to any device capable of being controlled by an electronic circuit or processor to display information in a visual or tactile. A display device may be configured as an input device taking input from a user or other system (e.g. a touch sensitive computer screen), or as an output device generating visual or tactile information, or the display device may configured to operate as both an input or output device at the same time, or at different times.

The output may be two-dimensional, three-dimensional, and/or mechanical displays and includes, but is not limited to, the following display technologies: Cathode ray tube display (CRT), Light-emitting diode display (LED), Electroluminescent display (ELD), Electronic paper, Electrophoretic Ink (E-ink), Plasma display panel (PDP), Liquid crystal display (LCD), High-Performance Addressing display (HPA), Thin-film transistor display (TFT), Organic light-emitting diode display (OLED), Surface-conduction electron-emitter display (SED), Laser TV, Carbon nanotubes, Quantum dot display, Interferometric modulator display (IMOD), Swept-volume display, Varifocal mirror display, Emissive volume display, Laser display, Holographic display, Light field displays, Volumetric display, Ticker tape, Split-flap display, Flip-disc display (or flip-dot display), Rollsign, mechanical gauges with moving needles and accompanying indicia, Tactile electronic displays (aka refreshable Braille display), Optacon displays, or any devices that either alone or in combination are configured to provide visual feedback on the status of a system, such as the "check engine" light, a "low altitude" warning light, an array of red, yellow, and green indicators configured to indicate a temperature range.

"Electronic funds transfer" generally refers to the electronic exchange or transfer of money from one account to another, either within a single financial institution or across multiple institutions, through computer-based systems. Examples include cardholder-initiated transactions, using a payment card such as a credit or debit card; direct deposit payment initiated by the payer; direct debit payments, sometimes called electronic checks, for which a business debits the consumer's bank accounts for payment for goods or services; wire transfer via an international banking network such as the Society for Worldwide Interbank Financial Telecommunication (SWIFT); electronic bill payment in online banking, which may be delivered by EFT or paper check; transactions involving stored value of electronic money, possibly in a private currency.

"Event" generally refers to an event where one or more participants engages in any sort of activity to determine a final ranking of participants relative to other participants engaging in the same event. The final ranking or outcome is generally calculated when the event is completed, although partial or interim rankings may be calculated as the event is occurring, particularly for longer events. Examples of "events" include various types of sporting events with individual participants competing directly against one another (e.g. a horse race, automobile race, tennis match, chess match, bridge match, and the like). Other events include sports events with multiple participants competing in groups as a team such as in baseball, cricket, soccer, American-style football, basketball, or relay races such as a 400 m relay performed in the context of a track-and-field or swimming competition.

Events commonly include competitive mental or physical activity which aim to use, maintain, or improve the competitors' physical or mental ability and skills while providing entertainment to participants and/or spectators. Many sports exist which include events occurring a different times and include events requiring only two participants to events with hundreds of simultaneous participants, either in teams or competing as individuals.

Sports and associated events are generally governed by a set of rules or customs which serve to provide for fair competition and a consistent method for determining a winner. Winning can be determined by physical events such as scoring goals or crossing a line first, or by the determination of judges who are scoring elements of the performance, including objective or subjective measures such as technical performance or artistic impression.

Records of performance are often kept and this information may be widely announced or reported. In addition, sports events are a major source of entertainment for non-participants. Some spectators may also place wagers on the outcome of a sporting event, or on the performance of an individual participant or team performing in a sports event.

"Horse race" generally refers to any race or other sporting event where horses participate in the event. In such events, horses may be listed as the participants in the event. Examples include, but are not limited to, Thoroughbred, Quarter horse, and Standardbred racing.

"Identifier" generally refers to a name that identifies (that is, labels the identity of) either a unique thing or a unique class of things, where the "object" or class may be an idea, physical object (or class thereof), or physical substance (or class thereof). The abbreviation "ID" often refers to identity, identification (the process of identifying), or an identifier (that is, an instance of identification). An identifier may or may not include words, numbers, letters, symbols, shapes, colors, sounds, or any combination of those.

The words, numbers, letters, or symbols may follow an encoding system (wherein letters, digits, words, or symbols represent ideas or longer identifiers) or they may simply be arbitrary. When an identifier follows an encoding system, it is often referred to as a code or ID code. Identifiers that do not follow any encoding scheme are often said to be arbitrary IDs because they are arbitrarily assigned without meaning in any other context beyond identifying something.

"Input Device" generally refers to any device coupled to a computer that is configured to receive input and deliver the input to a processor, memory, or other part of the computer. Such input devices can include keyboards, mice, trackballs, touch sensitive pointing devices such as touchpads, or touchscreens. Input devices also include any sensor or sensor array for detecting environmental conditions such as temperature, light, noise, vibration, humidity, and the like.

"Memory" generally refers to any storage system or device configured to retain data or information. Each memory may include one or more types of solid-state electronic memory, magnetic memory, or optical memory, just to name a few. Memory may use any suitable storage technology, or combination of storage technologies, and may be volatile, nonvolatile, or a hybrid combination of volatile and nonvolatile varieties. By way of non-limiting example, each memory may include solid-state electronic Random Access Memory (RAM), Sequentially Accessible Memory (SAM) (such as the First-In, First-Out (FIFO) variety or the Last-In-First-Out (LIFO) variety), Programmable Read Only Memory (PROM), Electronically Programmable Read Only Memory (EPROM), or Electrically Erasable Programmable Read Only Memory (EEPROM).

Memory can refer to Dynamic Random Access Memory (DRAM) or any variants, including static random access memory (SRAM), Burst SRAM or Synch Burst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (REDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM).

Memory can also refer to non-volatile storage technologies such as non-volatile read access memory (NVRAM), flash memory, non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Domain Wall Memory (DWM) or "Racetrack" memory, Nano-RAM (NRAM), or Millipede memory. Other non-volatile types of memory include optical disc memory (such as a DVD or CD ROM), a magnetically encoded hard disc or hard disc platter, floppy disc, tape, or cartridge media. The concept of a "memory" includes the use of any suitable storage technology or any combination of storage technologies.

"Module" or "Engine" generally refers to a collection of hardware computational or logic circuits, or to a series of logic or computational instructions expressed in executable, object, or source code, or any combination thereof, configured to perform certain tasks or functions. A module may be implemented in software maintained in volatile memory in a computer and executed by a processor or other circuit. A module may be implemented as software stored in an erasable/programmable nonvolatile memory and executed by a processor or processors. A module may be implanted as software coded into an Application Specific Information Integrated Circuit (ASIC), or the module may also be a collection of digital or analog circuits configured to operate according to the desired outcome.

"Multiple" as used herein is synonymous with the term "plurality" and refers to more than one, or by extension, two or more.

"Network" or "Computer Network" generally refers to a telecommunications network that allows computers to exchange data. Computers can pass data to each other along data connections by transforming data into a collection of datagrams or packets. The connections between computers and the network may be established using either cables, optical fibers, or via electromagnetic transmissions such as for wireless network devices.

Computers coupled to a network may be referred to as "nodes" or as "hosts" and may originate, broadcast, route, or accept data from the network. Nodes can include any computing device such as personal computers, phones, servers as well as specialized computers that operate to maintain the flow of data across the network, referred to as "network devices". Two nodes can be considered "networked together" when one device is able to exchange information with another device, whether or not they have a direct connection to each other.

Examples of wired network connections may include Digital Subscriber Lines (DSL), coaxial cable lines, or optical fiber lines. The wireless connections may include BLUETOOTH, Worldwide Interoperability for Microwave Access (WiMAX), infrared channel or satellite band, or any wireless local area network (Wi-Fi) such as those implemented using the Institute of Electrical and Electronics Engineers' (IEEE) 802.11 standards (e.g. 802.11(a), 802.11 (b), 802.11(g), or 802.11(n) to name a few). Wireless links may also include or use any cellular network standards used to communicate among mobile devices including 1G, 2G, 3G, or 4G. The network standards may qualify as 1G, 2G, etc. by fulfilling a specification or standards such as the specifications maintained by International Telecommunication Union (ITU). For example, a network may be referred to as a "3G network" if it meets the criteria in the International Mobile Telecommunications-2000 (IMT-2000) specification regardless of what it may otherwise be referred to. A network may be referred to as a "4G network" if it meets the requirements of the International Mobile Telecommunications Advanced (IMTAdvanced) specification. Examples of cellular network or other wireless standards include AMPS, GSM, GPRS, UMTS, LTE, LTE Advanced, Mobile WiMAX, and WiMAX-Advanced.

Cellular network standards may use various channel access methods such as FDMA, TDMA, CDMA, or SDMA. Different types of data may be transmitted via different links and standards, or the same types of data may be transmitted via different links and standards.

The geographical scope of the network may vary widely. Examples include a body area network (BAN), a personal area network (PAN), a local-area network (LAN), a metropolitan area network (MAN), a wide area network (WAN), or the Internet.

A network may have any suitable network topology defining the number and use of the network connections. The network topology may be of any suitable form and may include point-to-point, bus, star, ring, mesh, or tree. A network may be an overlay network which is virtual and is configured as one or more layers that use or "lay on top of" other networks.

A network may utilize different communication protocols or messaging techniques including layers or stacks of protocols. Examples include the Ethernet protocol, the internet protocol suite (TCP/IP), the ATM (Asynchronous Transfer Mode) technique, the SONET (Synchronous Optical Networking) protocol, or the SDE1 (Synchronous Digital Elierarchy) protocol. The TCP/IP internet protocol suite may include application layer, transport layer, internet layer (including, e.g., IPv6), or the link layer.

"Odds" generally refers to a numerical expression indicating a ratio of the amounts staked by parties on opposite sides of a wager, or the amounts an odds maker is predicting will be staked by parties on opposing sides of a wager.

For example, the odds may be 2-1 of a participant finishing an event with a final ranking of 1 (i.e., the highest finishing position). This indicates that the possibility that this participant would achieve that highest rank merits a return to the bettor of $2 in winnings for every $1 wagered. In a pari-mutuel pool environment, this would mean that if the participant finishes the event with the highest ranking, a bet of $2 would return a payout of $6$4 in winnings plus the original stake of $2. In another example, if the odds of the participant finishing with the highest ranking are 1-1, a $2 bet would return a payout of $4 ($2 in winnings plus the original $2 bet). In yet another example, at 3-1 odds of finishing with the highest ranking, a $2 bet would return $8 ($6 in winnings plus the original $2 bet) if that participant were to finish in the highest position.

"Output Device" generally refers to any device or collection of devices that is controlled by computer to produce an output. This includes any system, apparatus, or equipment receiving signals from a computer to control the device to generate or create some type of output. Examples of output devices include, but are not limited to, screens or monitors displaying graphical output, any projector a projecting device projecting a two-dimensional or three-dimensional image, any kind of printer, plotter, or similar device producing either two-dimensional or three-dimensional representations of the output fixed in any tangible medium (e.g. a laser printer printing on paper, a lathe controlled to machine a piece of metal, or a three-dimensional printer producing an object). An output device may also produce intangible output such as, for example, data stored in a database, or electromagnetic energy transmitted through a medium or through free space such as audio produced by a speaker controlled by the computer, radio signals transmitted through free space, or pulses of light passing through a fiber-optic cable.

"Personal computing device" generally refers to a computing device configured for use by individual people. Examples include mobile devices such as Personal Digital Assistants (PDAs), tablet computers, wearable computers installed in items worn on the human body such as in eye glasses, laptop computers, portable music/video players, computers in automobiles, or cellular telephones such as smart phones. Personal computing devices can be devices that are typically not mobile such as desk top computers, game consoles, or server computers. Personal computing devices may include any suitable input/output devices and may be configured to access a network such as through a wireless or wired connection, and/or via other network hardware.

"Pari-mutuel betting" generally refers to a betting system in which all bets of a particular type are placed together in a common pool (or multiple separate common pools). Taxes and the "house-take" or "take-out" are removed, and payoff odds are calculated by sharing the common pool among all winning bets. A totalizator can be used to manage the odds, pools, payouts, and other aspects of pari-mutuel betting.

Pari-mutuel betting differs from "fixed-odds betting" in that the final payout varies based on the size of the pool and the amounts wagered on various outcomes. In contrast, with fixed odds betting, the payout is agreed at the time the bet is made.

"Processor" generally refers to one or more electronic components configured to operate as a single unit configured or programmed to process input to generate an output. Alternatively, when of a multi-component form, a processor may have one or more components located remotely relative to the others. One or more components of each processor may be of the electronic variety defining digital circuitry, analog circuitry, or both. In one example, each processor is of a conventional, integrated circuit microprocessor arrangement, such as one or more PENTIUM, i3, i5 or i7 processors supplied by INTEL Corporation of Santa Clara, Calif., USA. Other examples of commercially available processors include but are not limited to the X8 and Freescale Coldfire processors made by Motorola Corporation of Schaumburg, Ill., USA; the ARM processor and TEGRA system on a chip (SoC) processors manufactured by Nvidia of Santa Clara, Calif., USA; the POWER7 processor manufactured by International Business Machines of White Plains, N.Y., USA; any of the FX, Phenom, Athlon, Sempron, or Opteron processors manufactured by Advanced Micro Devices of Sunnyvale, Calif., USA; or the Snapdragon SoC processors manufactured by Qalcomm of San Diego, Calif., USA.

A processor also includes Application-Specific Integrated Circuit (ASIC). An ASIC is an Integrated Circuit (IC) customized to perform a specific series of logical operations is controlling a computer to perform specific tasks or functions. An ASIC is an example of a processor for a special purpose computer, rather than a processor configured for general-purpose use. An application-specific integrated circuit generally is not reprogrammable to perform other functions and may be programmed once when it is manufactured.

In another example, a processor may be of the "field programmable" type. Such processors may be programmed multiple times "in the field" to perform various specialized or general functions after they are manufactured. A field-programmable processor may include a Field-Programmable Gate Array (FPGA) in an integrated circuit in the processor. FPGA may be programmed to perform a specific series of instructions which may be retained in nonvolatile memory cells in the FPGA. The FPGA may be configured by a customer or a designer using a hardware description language (HDL). In FPGA may be reprogrammed using another computer to reconfigure the FPGA to implement a new set of commands or operating instructions. Such an operation may be executed in any suitable means such as by a firmware upgrade to the processor circuitry.

Just as the concept of a computer is not limited to a single physical device in a single location, so also the concept of a "processor" is not limited to a single physical logic circuit or package of circuits but includes one or more such circuits or circuit packages possibly contained within or across multiple computers in numerous physical locations. In a virtual computing environment, an unknown number of physical processors may be actively processing data, the unknown number may automatically change over time as well.

The concept of a "processor" includes a device configured or programmed to make threshold comparisons, rules comparisons, calculations, or perform logical operations applying a rule to data yielding a logical result (e.g. "true" or "false"). Processing activities may occur in multiple single processors on separate servers, on multiple processors in a single server with separate processors, or on multiple processors physically remote from one another in separate computing devices.

"Replay" generally refers to presenting a representation of a past event using any suitable technology. A replay may involve rendering and/or displaying a video recording of the event that may include actual footage of the event as it occurred in the past. A replay may include rendering and/or displaying an animated representation of the event or the outcome of the event, or any other later recreation of the event after it has taken place. Digital, analog, or computer generated representations may be rendered using any suitable technology or devices, or by any combination thereof. A replay may include audible representations of the event results as well such as recorded audio that may be integrated with or separate from a video or other graphical representation.

"Scratch" generally refers to removing a participant from an event before the event occurs. For example, a horse is said to "scratch" from a horse race if the horse is removed from the lineup before the race is run.

"Statistical odds" generally refers to a numerical expression of the chance of a predicted outcome occurring. Odds in statistics are sometimes represented as a percentage, decimal number, or in a written form. For example, the odds of rolling a two with a fair die may be expressed as being about 16.7%, 0.166666, or simply "one chance in six. "Odds against" may be used to express the likelihood that a particular event will not take place.

"Terminal" generally refers to a device or assembly of multiple devices that a user directly interacts with in order to make assets (e.g. money) available for making bets, placing the actual bets themselves, and otherwise managing the betting process. Examples of terminals include machines with any suitable combination display devices, input devices, processors, memory, and bill acceptors for taking money to wager. Such machines may be located in a betting facility at a location where the events bettors are betting on are currently taking place, or have taken place in the past (e.g. a horse racing track in the case of betting on horse racing, or casino in the case of events such as boxing matches that take place in the casino). These devices may be configured to manage the betting process, or may execute software configuring the device to facilitate the betting process.

Another example of a terminal is a personal or handheld computing device such as a smart phone, tablet, a desktop or laptop personal computer, and the like, executing software configuring the device to facilitate the betting process. Such devices may include or be coupled to processors, memory, and/or input, output, and display devices such as keyboards, mice, printers, barcode scanners, and various kinds of touch sensitive devices such as a touch sensitive display device, or a separate touch sensitive pad. Such devices may include a network interface or other networking hardware controlled by the processor that allows the device to be coupled to a computer network either wirelessly or through any other suitable device or media. Devices with these features or attached equipment may collectively be considered a "terminal" where the devices include software configured to execute the betting process. In this example, the terminal may also be remote from the location where the event being bet is taking place, or has already taken place in the past.

"Totalizator" or "Totalisator" generally refers to a system that may include hardware, software, communications equipment, input, output, and other electronic devices configured to accept and process the cashing of wagers, calculate the odds and prices of the wagers, and record, display, and store pari-mutuel wagering information.

A totalizator system may include the following aspects:
1. Collecting bets from players (registers bets), for example, from wagering terminals.
2. Separating player bets into a commission for the operator and multiple prize pools for players to win (depending on the wager and math model chosen by the player).
3. Awarding winning players an amount of the appropriate prize pool commensurate with the winning event achieved by the player (and divides total amount bet among those who won).
4. Maintaining records of pari-mutuel wager events, outcomes, and activity.
5. Providing accounting reports and management terminals to manage all aspects of the system.

"Wager" or "bet" generally refers to an amount of money or other valuable asset intentionally put at risk by the better with the intention of receiving a return of assets with a value in excess of the amount initially put at risk. "Wagering" or "betting" thus generally refers to any process by which a wager or bet is made, and the results calculated. Wagering generally includes the better making a prediction as to an outcome that either has not yet materialized, or has already materialized but is unknown to the bettor. If the outcome matches the prediction made by the bettor turns out to be correct, the result of placing the wager is to return to the bettor assets whose value generally exceeds the value of the asset put at risk. This "return" or "payout" may be accepted as physical currency such as actual paper money, casino chips or types of vouchers that can later be redeemed for actual currency, or by an electronic funds transfer into an account maintained by the bettor. If the predicted outcome does not turn out to be correct, the bettor generally loses some or all of the initial wager.

A wager may be placed based on any of a wide variety of outcomes such as the score of a particular sporting event, the performance of members of the team of participants participating in a sporting event, the position of individual competitors participating in an event such as a horse race, dog race, automobile race, and the like. Wagering may take place in the facility where the event is occurring (e.g. a track where horseracing is or has taken place), or wagers may be placed in one location based on events occurring, or that have occurred, in a separate geographical location.

The invention claimed is:
1. A method, comprising:
controlling an input device to accept a wager amount defining an amount of a currency to wager, wherein the input device is controlled by a processor;

using the processor to initiate a transfer of the amount of currency to wager into a common prize pool;

using the processor to query a database to automatically retrieve data about multiple separate events that occurred in the past that included multiple different participants, wherein the data about the events includes a final ranking for each of the different participants, the final ranking indicating the outcome for each of the different participants with respect to other participants who competed in the same event of the multiple separate events;

controlling the input device to accept a combination of predicted rankings for each of the multiple different participants of the multiple separate events using the processor, the combination of predicted rankings indicating a predicted final ranking for each participant competing in the multiple separate events;

calculating a final score using the processor, wherein the processor combines together the predicted rankings for each of the multiple separate events, and wherein the final score is calculated based on combinations of differences between each of the predicted rankings and each of the corresponding final rankings for each participant of the multiple separate events;

calculating a prize amount using the processor, wherein the prize amount is a currency amount calculated using the final score and the wager input;

using the processor to initiate a transfer of the prize amount out of the common prize pool when the prize amount is greater than zero; and rendering an animated replay of at least one of the multiple separate events using the processor, wherein the animated replay includes a graphical representation of at least a portion of the data about the multiple different participants;

using the processor to control a display device to display an animated replay of at least one of the multiple separate events.

2. The method of claim 1, comprising:
calculating a pre-event ranking for the participants using the processor, wherein the pre-event ranking is calculated based on individual odds of the participants attaining the highest ranking for their respective events.

3. The method of claim 2, wherein the data about multiple separate events includes the individual odds of the participants attaining the highest ranking for their respective events that was determined before the respective events occurred in the past.

4. The method of claim 1, wherein the events are horse races, wherein the participants are horses, wherein the predicted ranking is the predicted order of finish for the horses in each of the horse races, and where the final ranking is the actual order of finish for the horses competing in their respective races.

5. The method of claim 1, wherein calculating the final score comprises:
generating a wager result by comparing the predicted ranking to the final ranking for each participant of each event using the processor.

6. The method of claim 5, wherein the wager result includes a first identifier for each participant in each event wherein the final ranking and predicted ranking match, and a second identifier for each participant in each event wherein the final ranking and predicted ranking do not match.

7. The method of claim 5, comprising:
assigning a probability of occurrence to the wager result by using the processor to query the data about the events to determine the frequency of the outcome represented by the wager result.

8. The method of claim 7, wherein the prize amount is calculated using the probability of occurrence assigned to the wager result, and wherein wager results with a probability below a predetermined threshold result in a zero prize amount.

9. The method of claim 1, wherein the data about the multiple separate events retrieved from the database is randomly selected from the events stored in the database.

10. The method of claim 1, wherein the act of accepting a wager amount includes accepting the amount of currency to wager into a bill acceptor controlled by the processor.

11. The method of claim 1, comprising:
using the processor to control the display device to display a replay of at least one of the multiple separate events on the display device.

12. The method of claim 1, wherein the number of events in the multiple separate events is at least 3.

13. The method of claim 1, wherein the events are dog races, wherein the participants are dogs, wherein the predicted ranking is a predicted order of finish for the dogs in each of the dog races, and wherein the final ranking is the actual order of finish for the dogs competing in their respective races.

14. The method of claim 1, comprising:
using the processor to control the display device to display the final rankings retrieved from the database for the respective multiple participants.

15. The method of claim 14, wherein accepting the predicted rankings includes accepting input changing the predicted final ranking on the display for at least one of the multiple participants.

16. The method of claim 1, wherein calculating the final score comprises:
using the processor to generate a pattern ID that uniquely identifies a combination of the differences between the predicted ranking and the final rankings.

17. The method of claim 16, wherein generating the pattern ID comprises:
a) inserting a "1" into the pattern ID for each predicted ranking that matches a final ranking;
b) inserting a "0" into the pattern ID for each predicted ranking that does not match a final ranking; and
performing actions "a" and "b" for each final ranking for each participant of each separate event.

18. The method of claim 16, wherein calculating a prize amount comprises:
querying a prize award database using the pattern ID as a key to determine the prize amount;
wherein the prize amounts are indexed in the prize award database by pattern ID.

19. The method of claim 18, comprising:
loading the prize award database with prize amounts associated with one or more pattern IDs, payout percentages, and bet levels;
wherein the prize amounts are associated with the pattern IDs in descending order with the highest pattern IDs associated with the highest prize amounts.

20. The method of claim 1, wherein the data about multiple separate events that occurred in the past includes data about horse races, wherein the participants are horses.

21. The method of claim 1, wherein the data about multiple separate events includes data about horse races with at least 4 horse fields.

22. The method of claim 1, wherein the data about multiple separate events includes data about horse races where no horses scratched from any of the races.

23. The method of claim 1, wherein the data about multiple separate events includes data about horse races where there were no dead heats.

24. The method of claim 1, wherein the data about multiple separate events includes data about horse races where there were no coupled entries.

25. The method of claim 1, wherein the data about multiple separate events includes data about horse races where all horses finished the races.

26. The method of claim 1, wherein the data about multiple separate events includes data about horse races where all horses had odds of winning that were greater than 0 at the time of the race.

27. The method of claim 1, wherein the data about multiple separate events includes data about horse races wherein facilities hosting the horse races were located within the borders of the United States.

28. The method of claim 1, comprising
displaying an arrangement of graphical symbols corresponding to the prize amount, the arrangement of graphical symbols displayed on a display device controlled by the processor, wherein the arrangement of graphical symbols corresponds to the prize amount.

29. The method of claim 1, wherein the data about the multiple separate events is retrieved together from the database using a single query.

30. A method, comprising:
controlling an input device to accept a wager amount defining an amount of a currency to wager, wherein the input device is controlled by a processor;
using the processor to automatically retrieve data about a collection of different events that occurred in the past from a database, the different events each having multiple participants, wherein the data about the different events includes actual final rankings based on outcomes of each of the multiple participants for each event;
controlling the input device to accept input defining a combination of predicted outcomes for each participant of the different events;
calculating a final score using the processor, wherein the final score is calculated based on differences between each of the predicted outcomes and each of the actual final rankings for all of the multiple participants of the different events;
rendering an animated replay of at least one of the different events using the processor, wherein the animated replay includes a graphical representation of at least a portion of the data about the multiple participants; and
using the processor to control a display device to display the animated replay of at least one of the different events.

31. The method of claim 30, comprising:
using the processor to initiate a transfer of the amount of currency to wager into a prize pool; and
using the processor to initiate a transfer of the prize amount out of the prize pool when the prize amount is greater than zero.

32. The method of claim 30, wherein the final score combines together the differences between the combination of predicted outcomes and the actual final rankings for the multiple participants from each of the different events.

33. The method of claim 30, wherein the events are horse races, wherein the participants are horses, wherein the predicted ranking is the predicted order of finish for the horses in each of the horse races, and where the final ranking is the actual order of finish for the horses competing in their respective races.

34. The method of claim 30, wherein calculating the final score comprises:
generating a wager result by comparing the predicted ranking to the final ranking for each participant of each event using the processor.

35. The method of claim 34, wherein the wager result includes a first identifier for each participant in each event wherein the final ranking and predicted ranking match, and a second identifier for each participant in each event wherein the final ranking and predicted ranking do not match.

36. The method of claim 34, comprising:
assigning a probability of occurrence to the wager result by using the processor to query the data about the events to determine the frequency of the outcome represented by the wager result.

37. The method of claim 34, wherein the prize amount is calculated using a probability of occurrence assigned to the wager result, and wherein wager results with a probability below a predetermined threshold result in a zero prize amount.

38. The method of claim 30, wherein the data about the different events retrieved from the database are randomly selected from the events stored in the database.

39. The method of claim 30, wherein the multiple different events includes at least three separate events, and wherein each separate event includes at least five individual participants.

40. The method of claim 30, comprising:
rendering an arrangement of graphical symbols corresponding to the final score using the processor; and
using the processor to control the display device to display the arrangement of graphical symbols.

41. The method of claim 30, wherein the data about the different events is retrieved together from the database using a single query.

42. The method of claim 30, wherein the act of accepting a wager amount includes accepting a credit card and withdrawing funds for the wager from the credit card.

43. The method of claim 30, wherein the data about different events that occurred in the past includes data about horse races, wherein the participants are horses.

44. The method of claim 30, wherein the data about different events includes data about horse races with at least 4 horse fields.

45. The method of claim 30, wherein the data about different events includes data about horse races where no horses scratched from any of the races.

46. The method of claim 30, wherein the data about different events includes data about horse races where there were no dead heats.

47. The method of claim 30, wherein the data about different events includes data about horse races where there were no coupled entries.

48. The method of claim 30, wherein the data about different events includes data about horse races where all horses finished the races.

49. The method of claim 30, wherein the data about different events includes data about horse races where all horses had odds of winning that were greater than 0 at the time of the race.

50. The method of claim 30, wherein the data about different events includes data about horse races wherein facilities hosting the horse races were located within the borders of the United States.

* * * * *